US007318927B2

(12) United States Patent
Perez et al.

(10) Patent No.: US 7,318,927 B2
(45) Date of Patent: Jan. 15, 2008

(54) RECOMBINANT POXVIRUS FOR CHIMERIC PROTEINS OF THE HUMAN IMMUNODEFICIENCY VIRUS

(75) Inventors: Enrique Iglesias Perez, C. Habana (CU); Dania M. Vazquez Blomquist, Ciudad Habana (CU); Carlos A. Duarte Cano, Ciudad Habana (CU)

(73) Assignee: Centro de Ingenieria Genetica y Biotecnologia, C. Habana (CU)

( * ) Notice: Subject to any disclaimer, the term of this patent is extended or adjusted under 35 U.S.C. 154(b) by 600 days.

(21) Appl. No.: 10/469,256

(22) PCT Filed: Feb. 22, 2002

(86) PCT No.: PCT/CU02/00001

§ 371 (c)(1),
(2), (4) Date: Aug. 27, 2003

(87) PCT Pub. No.: WO02/068654

PCT Pub. Date: Sep. 6, 2002

(65) Prior Publication Data

US 2004/0073008 A1 Apr. 15, 2004

(30) Foreign Application Priority Data

Feb. 28, 2001 (CU) ........................................ 57/01

(51) Int. Cl.
*A61K 39/21* (2006.01)

(52) U.S. Cl. .............................. 424/188.1; 424/202.1; 424/208.1; 536/23.72

(58) Field of Classification Search ............ 424/188.1, 424/208.1, 192.1
See application file for complete search history.

(56) References Cited

U.S. PATENT DOCUMENTS 5,174,993 A 12/1992 Paoletti
5,505,941 A 4/1996 Paoletti

FOREIGN PATENT DOCUMENTS

| | | |
|---|---|---|
| EP | 0412766 | 2/1991 |
| WO | WO9821354 | 5/1998 |

OTHER PUBLICATIONS

Capsoni, F., et al., 1992, Membrane expression and function of complement receptors CR1 and CR3 on neutrophils from HIV-infected subjects: modulation by rTNF-alpha and rGM-CSF, Scand. J. Immunol. 36(4):541-546 (abstract provided).*

Parker, S. F., et al., 1997, Distinct domains of adenovirus EIA interact with specific cellular factors to differentially modulate human immunodeficiency virus transcription, J. Virol. 71(3):2004-2012.*

Manuel, L., et al., 2006, Identification and characterization of the chromatin-binding domains of the HIV-1 integrase interactor LEDGF/p. 75, J. Mol. Biol. 360(4):760-773.*

Hanke Tomas et al., "Effective Induction of Simian Immunodeficiency Virus-Specific Cytotoxic T Lymphocytes in Macaques by Using a Multiepitone Gene and DNA Prime-Modified Vaccinia Virus Ankara Boost Vaccination Regimen", *Journal of Virology*, vol. 73, No. 9, pp. 7524-7532 (1999).

Duarte Carlos A. et al., "Epitope Mapping, V-Region DNA Sequence, and Neutralizing Fab Fragments of Two Monoclonal antibodies Against the HIV-1 V3 Loop", *Immunotechnology*(*Amsterdam*), vol. 2, No. 1, pp. 11-20 (1996).

Whitton J. Lindsay et al., "A "String-of-Beads" Vaccine, Comprising Linked Minigenes, Confers Protection from Lethal Dose Virus Challenge", *Journal of Virology*, vol. 67, No. 1, pp. 348-352 (1993).

* cited by examiner

*Primary Examiner*—Jeffrey S. Parkin
(74) *Attorney, Agent, or Firm*—Hoffman & Baron, LLP

(57) ABSTRACT

The invention relates to HIV chimeric gene formed by the union of fragments of different genes of said virus, wherein said fragments contains epitopes for cytotoxic T cells (CTL) or HIV-1 auxiliary T cells, which are presented by a wide range of antigens of type Major Histocompatibility Complex (HLA-I). Recombinant poxviruses are obtained from said genes, which are useful for prophylactic and therapeutic vaccination against HIV/AIDS infections, are capable of generating a protective immune cell response in vaccinated laboratory animals and are recognized by the CTL lymphocytes of HIV/AIDS patients.

1 Claim, 7 Drawing Sheets

RECOMBINANT POXVIRUS FOR CHIMERIC PROTEINS OF THE HUMAN IMMUNODEFICIENCY VIRUS

This application is a U.S. National Phase Application of International Application No. PCT/CU02/00001 filed on Feb. 22, 2002. The specification of International Application No. PCT/CU02/00001 is hereby incorporated by reference.

This application asserts priority to Cuban Application No. CU 57/2001 filed on Feb. 28, 2001. The specification of Cuban application No. CU 57/2001 is hereby incorporated by reference.

FIELD OF THE INVENTION

The present invention is related to the field of immunology and in particular with the development of vaccines for the prevention or treatment of Acquired Immunodeficiency Syndrome (AIDS). Chimeric genes and Fowlpox Viruses expressing thereof, useful for the treatment and prevention of AIDS are disclosed.

BACKGROUND OF THE INVENTION

HIV is the etiological agent of AIDS (Popovic M, Sarngadharan M, Read G, and Gallo R C. Science 1984, 224: 497-500). This virus infects not only CD4+T cells (Klatzman D, Barre Sinoussi F, Nugeyre M T, Dauguet C, Vilmer E, Griscelli C, Brun-Vezinet F, Rouzioux C, Gluckman, J D, Chermannn J C and Montagnier L. Science 1984, 225:59-63) but also other cell types such as macrophages, dendritic cells, microglia and epithelial cells.

HIV can escape from the host immune response in spite of the high levels of antibodies that persists through all the infection. At the long term, HIV causes profound immunodeficiency in the host, which becomes highly susceptible to the attack of opportunistic infections.

More than 36 millions persons are living with HIV/AIDS and 94% of the 16 000 daily infections occur in developing countries. (UNAIDS. Report on the global HIV/AIDS epidemic, June 2000). Due to these alarming figures and the absence of an effective and affordable treatment for this disease, there is an urgent need for the development of an HIV vaccine.

Among several characteristics of HIV that difficult this task the more important is perhaps the high degree of genetic variability of its antigens, especially the envelope glycoproteins (gp160) where the main domains involved in the infectious process and targeted by neutralizing antibodies are located.

Vaccine candidates based on neutralizing antibodies have been able to protect against HIV in chimpanzees (Berman P W, Gregory T J, Lavon R, Nakamura G R, Champe M A, Porter J P, Wurm F M, Hershberg R D, Cobb G K and Eichberg J W. Nature 1990, 345: 622-625; Girard M, Kieny M P, Pinter A; Barre-Sinoussi F, Nara P, Kolbe H, Kusumi K, Chaput A, Rainhart T, Muchmore E, Ronco J, Kaczorek M, Gomard E, Gluckman J C and Fultz P N, PNAS 1991, 88: 542-546). However those experiments were performed in nearly ideal conditions where the dose, route and timing of the viral challenge were very different from natural infection. Moreover, those immunogens can't protect against divergent HIV isolates and the antibodies raised fail to neutralize primary HIV isolates.

Different vaccine candidates have been evaluated in Phase I and II clinical trials (Johnston M I. AIDS vaccine development: status and future directions. 1999. XII Colloque des Cent Gardes. Ed. Girard M and Dodet B.161-163). Most of these are based on the envelope proteins: gp160 and gp120. Only one vaccine, based on recombinant gp120 is currently undergoing efficacy evaluation in Phase III trials in Thailand and USA. Results from previous trials suggested that only very limited protection if any can be expected from this vaccine.

Due to these serious limitations to generate a humoral response able to confer protection against different HIV isolates and subtypes, the efforts of the investigators have mostly switched in the last years toward the development of vaccine candidates capable of stimulate mainly the cellular branch of the immune system and particularly cytotoxic T cells directed against HIV antigens.

Among the experimental findings that strongly suggest the clinical relevance of anti HIV CTIs are: The administration of anti CD8 monoclonal antibody to macaques previously inoculated with Simian-Human Immunodeficiency Virus (SHIV) markedly enhanced the levels of viremia (Matano T, Shibata R, Simeón C, Connors M, Lane C, Martin M, Administration of an Anti-CD8 monoclonal antibody interferes with the clearance of chimeric Simian/Human Immunodeficiency virus during primary infections of rhesus macaques, J Virol, 1998, 72, 1: 164-169); viral variants able to escape CD8+ T cell recognition are selected in both HIV-infected individuals (Borrow, P., H. Lewicki, X. Wei, M. S. Horwitz, N. Peffer, H. Meyers, J. A. Nelson, J. E. Gairin, B. H. Hahn, M. B. A. Oldstone, and G. M. Shaw. 1997. Antiviral pressure exerted by HIV-1-specific cytotoxic T lymphocytes (CTLs) during primary infection demonstrated by rapid selection of CTL escape virus. Nature Med. 3:205-211.) and SIV-infected macaques (Allen, T. M., O. C. D H, P. Jing, J. L. Dzuris, B. R. Mothe, T. U. Vogel, E. Dunphy, M. E. Liebl, C. Emerson, N. Wilson, K. J. Kunstman, X. Wang, D. B. Allison, A. L. Hughes, R. C. Desrosiers, J. D. Altman, S. M. Wolinsky, A. Sette, and D. I. Watkins. 2000. Tat-specific cytotoxic T lymphocytes select for SIV escape variants during resolution of primary viraemia. Nature. 407:386-90); SCID mice populated with PBMC from volunteers injected with HIV-1 recombinant Vaccinia Virus (VV) were protected against challenged in the absence of neutralizing antibodies (Van Kuyk R, Torbett B, Gulizia R et al, Human CTL specific for the nef protein of HIV protect hu-PBL-SCID mice from HIV infection. AIDS Res Hum Retroviruses, 1993; 9 (suppl 1:S77); a significant proportion of exposed uninfected persons display cellular immune response specific for HIV proteins, this is true for African sex workers (Rowland-Jones S L, J Sotton, K Ariyoshi, T Dong, F Gotch, s McAdams, D Whitby, S Sabally, A Gallimore, T Corrah, M Takiguchi, T Schltz, A McMichael, H Whittle. 1995. HIV-specific cytotoxic T cells in HIV-exposed but uninfected Gambian women. Nature Medicine, 1: 59-64) and children born from seropositive mothers (Rowland-Jones S L, D F Nixon, M C Aldhous, F Gotch, K Aroyoshi, N Hallam, J S Kroll, K Froebel, A McMichael. HIV specific cytotoxic T-cell activity in an HIV-exposed but uninfected infant. Lancet, 1993, 341: 860-861). Additionally long term non progressors exhibit a strong CTL response (Cao, Y, Qin L, Zhang I, Safrit J and Ho D D, New Engl J Med, 1995, 332:201-208; Riviere Y, McChesney M B, Porrot E, et al. AIDS Res Hum Retroviruses, 11:903-990); and the HLA class I type has been associated with the rate of disease progression in HIV-1-infected individuals (Carrington, M., G. W. Nelson, M. P. Martin, T. Kissner, D. Vlahov, J. J. Goedert, R. Kaslow, S. Buchbinder, K. Hoots, and O. B. S J. 1999. HLA and HIV-1: heterozygote advantage and B*35-Cw*04 disadvantage.

Science. 283:1748-52). The CTL response precede the neutralizing antibodies in the natural infection and has been associated with the control of viremia in acute infection (Koup R A, Safrit J T, Cao Y, et al, Temporal association of cellular immune responses with the initial control of viremia in primary human immunodeficiency syndrome, J Virol, 1994; 68: 4650-4655) and progression to AIDS correlates strongly with the impairment of CTL activity. (Harrer T, Harrer E, Kalams S, Elbeik T, Staprans S, Feinberg M B, Cao Y, Ho D D, Yilma T, Caliendo A, Jonson R P, Buchbinder S, and Walker B. HIV-specific CTL-response in healthy long-term asymptomatic HIV infection. AIDS Res Hum Retroviruses, 1996, 12, 7: 585-592). Finally vaccines that induce virus-specific CD8+ T cell responses can favorably affect the outcome of infection in SIV models of HIV infection (Barouch, D. H., S. Santra, J. E. Schmitz, M. J. Kuroda, T. M. Fu, W. Wagner, M. Bilska, A. Craiu, X. X. Zheng, G. R. Krivulka, K. Beaudry, M. A. Lifton, C. E. Nickerson, W. L. Trigona, K. Punt, D. C. Freed, L. Guan, S. Dubey, D. Casimiro, A. Simon, M. E. Davies, M. Chastain, T. B. Strom, R. S. Gelman, D. C. Montefiori, M. G. Lewis, E. A. Emini, J. W. Shiver, and N. L. Letvin. 2000. Control of viremia and prevention of clinical AIDS in rhesus monkeys by cytokine-augmented DNA vaccination. Science. 290:486-92; Gallimore, A., M. Cranage, N. Cook, N. Almond, J. Bootman, E. Rud, P. Silvera, M. Dennis, T. Corcoran, J. Stott, A. McMichael, and F. Gotch. 1995. Early suppression of SIV replication by CD8+ nef-specific cytotoxic T cells in vaccinated macaques. Nature Med. 1:1167-1173.)

All this body of experimental findings strongly suggest that therapeutic and prophylactic strategies should include the induction/preservation/restoration of this arm of the immune response as at least one of their goals.

Different methodologies have been developed to generate CTLs in animals or humans. The most effective so far has been the recombinant live vectors. This method uses harmless viruses or bacteria to transport selected genes from the pathogen into the cells of the recipient to produce there the selected antigens. This procedure of gene delivering into cells maximizes the processing of CTL epitopes and their presentation by MHC-I molecules and subsequently the efficient stimulation of CTL clones in the host.

The viruses that have been more successfully used as vectors have been the poxviruses (Poxyiridae family). The best-known member of this family is Vaccinia Virus (VV), which was extensively used in humans during smallpox eradication campaign.

Several clinical trials has been carried out with VV recombinant for HIV proteins (Corey L, McElrath J, Weihold K, Matthewa T, Stablein D, Grahm B, Keefer M, Schwartz D, Gorse G. Cytotoxic T Cell and Neutralizing Antibody Responses to Human Immunodeficiency Virus Type 1 Envelope with a combination vaccine regimen. J Infectious Dis, 1998, 177:301-9; Graham B S, Matthews T J, Belshe R, Clements M L, Dolin R, Wright P F, Gorse G J, Schwartz D H, Keefer M C, Bolognesi D P, Corey L, Stablein D, Esterlitz J R, Hu S L, Smith G E, Fast P, Koff W, J Infectious Dis, 1993, 167: 533-7). However, VV has two main limitations for human use: (1) A small percentage of vaccinated persons showed strong adverse reactions that can be lethal in the case of immune-compromised individuals (2) persons with previous history of VV vaccination respond poorly against heterologous antigens.

A solution to these drawbacks has been the use of Avipoxvirus instead of VV. These are members of the poxvirus family but their replication is restricted to avian cells and its replication cycle is abortive in human cells. Two Avipoxviruses have been used with these purposes: Canarypox Virus (CPV) and Fowlpox Virus (FPV).

Avipoxviruses recombinants for various human pathogens of tumor-associated antigens induce CTL response in animals (Limbach K J, and E Paoletti. 1996. Non-replicating expression vectors: applications in vaccines development and gene therapy. Epidemiol. Infect. 116:241-256). The use of recombinant Avipoxvirus for vaccine development has been patented in USA (Paoletti E. y cols 1992 U.S. Pat. No. 5,174,993, Paoletti E. et al 1993, U.S. Pat. No. 5,505,941) and specifically a patent application on the use of recombinant avipoxviruses for lentiviral antigens has been presented in Europe. (Paoletti E et al, EP0956360)

A CPV recombinant for HIV-1 gag, pol and env has been evaluated in Phase I and II trials in healthy volunteers (Clements-Mann M L, K Weinhold, T J Matthews, B S Graham, G L Gorse, M C Keefer, M J McElrath, R-H Hsieh, J Mestecky, S Zolla-Pazner, J Mascola, D Schwartz, R Siliciano, L Corey, P F Wright, R Belshe, R Dolin, S Jackson, S Xu, P Fast, M C Walker, D Stablein, J-L Excler, J Tartaglia, A-M Duliege, F Sinangil, E Paoletti. 1998. Immune responses to Human Immunodeficiency Virus (HIV) Type 1 induced by Canarypox expressing HIV-1MN gp120, HIV-1SF2 recombinant gp120, or both vaccines in seronegative adults. J Infect Dis 177: 1230-1246; Egan M A, W A Pavlat, J Tartaglia, E Paoletti, K J Weinhold, M L Clements, R F Siliciano. 1995. Induction of Human Immunodeficiency Virus Type 1 (HIV-1)-specific cytolytic T lymphocyte responses in seronegative adults by a nonreplicating, host-range-restricted canarypox vector (ALVAC) carrying the HIV-1MN env gene. J Infect Dis 171: 1623-1627). CTLs against at least one HIV antigen were reported in the 50% of vaccinated in a Phase I trial, 30% in a Phase II trial and less than 10% in the last Phase I trial in Uganda. This rCPV (vCP205) was created trough the insertion of HIV genes in three different non-essential regions in the genome to achieve a CTL response against more than one HIV target.

In the other hand FPV has been also used to induce a CTL response in macaques against HIV antigens in combination with DNA immunization. (Robinson H L, D C Montefiori, R P Johnson, K H Manson, M L Kalish, J D Lifson, T A Rizvi, S Lu, S-L Hu, G P Mazzara, D L Panicali, J G Herndon, R Glickmanm, M A Candido, S L Lydy, M S Wyand and H M McClure. 1999. Nature Medicine, 5: 526-534). This combination of immunogens provided some level of protection in the HIV-1/macaca nemestrina infection model (Kent S J, A Zhao, S J Best, J D Chandler, D B Boyle, I A Ramshaw. Enhanced T-Cell immunogenicity and protective efficacy of a human immunodeficiency virus type 1 vaccine regime consisting of a consecutive priming with DNA and boosting with recombinant fowlpox virus. 1998. J Virol, 72: 10180-10188). However this animal model present important limitations since HIV infection in *M nemestrina* is inefficient and difficult to reproduce.

It has also been reported the generation of a CTL response through the immunization with minigenes composed of a series of exact CTL epitopes from several pathogens (Whitton, L, Sheng N, Oldstone M B, and McKee T. A "string of beads" vaccine, comprising linked minigenes, confers protection from lethal-dose virus challenge, J Virol, 1993, 67, 1:348-352; A multivalent minigene vaccine, containing B-cell, cytotoxic T-Lymphocyte and Th epitopes from several microbes, induces appropriate responses in vivo and confers protection against more than one pathogen. J Virol, 71, 3: 2292-2302).

Modified Vaccinia Ankara (MVA) recombinant for a gag derived minigene together with the whole gag gene has been used to induce a CTL response in mice (Hanke T, R V Samuel, T J Blanchard, V C Neumann, T M Allen, J E Boyson, S A Sharpe, N Cook, G L Smith, D I Watkins, M P Cranage, A J McMichael. 1999. Effective induction of simian immunodeficiency virus-specific cytotoxic T lymphocytes in macaques by using a multiepitope gene and DNA prime-Modified Vaccinia Virus Ankara boost vaccination regimen. J Virol, 73, 9: 7524-7532). Those minigenes consist of a string of discrete CTL epitopes from gag.

The main limitation of the minigene approach is that the combination of individual CTL epitopes only covers a limited range of HLA antigens and therefore the CTL response elicited is by definition to much restricted.

DETAILED DESCRIPTION OF THE INVENTION

The essence of the present invention is the construction of chimeric genes composed by CTL epitopes rich regions from HIV proteins, where those regions are selected from both, internal conserved proteins and regulatory proteins expressed very early in the viral life cycle.

This solution has advantages over the described HIV minigenes because allows the simultaneous processing of overlapping CTL epitopes presented by many HLA alleles. Another advantage of this solution in comparison to other avipoxvirus recombinant for several HIV-1 proteins is that the concentration of immunologically relevant regions from several proteins in a single gene facilitates the generation of recombinant viruses, and avoid the necessity to use several antibiotic resistance systems in the same recombinant virus. Additionally it facilitates the combination of epitopes from several HIV subtypes in a single recombinante virus. The chosen regions belong to the most conserved viral proteins and to early expressed regulatory products. Those CTL epitopes rich regions are combined with conserved T helper cells epitopes flanked by two lysines to facilitate their processing by cellular proteases. Finally a B cell epitope, recognized by a monoclonal antibody, is added to facilitate the detection of the polypeptide by immunochemical techniques.

The chimeric gene is assembled by joining together different DNA fragments, some of them generated by chemical synthesis and others amplified by Polimerase Chain Reaction (PCR) using HIV genes as templates. The DNA fragments are cloned together in an appropriate plasmid vector, sequenced and translated to a poxvirus recombination vector.

More particularly, this invention refers to the gene cr3, which contains Th cells epitopes from HIV-1 proteins gp120, gp41 and Vpr, the epitope on the V3 loop of gp120 recognized by Mab 2C4 (Duarte C A, Pérez L, Vázquez J, Dueñas M, Vilarubia O L, Navea L, Valdés R, Reyes O, Montero M, Ayala M, and Gavilondo J. Epitope mapping, V region DNA sequence, and neutralizing Fab fragments of two monoclonal antibodies against the HIV-1 V3 loop. Immunotechnology 1996, 2:11-20) and CTL epitopes rich regions on proteins RT, Gag and Nef.

Those chimeric genes are inserted in the genome of a bacterial or viral lived vector (ej poxvirus, herpesvirus, alphavirus, poliovirus, adenovirus, BCG, *Salmonella*), being this vector preferentially a poxvirus, and still more specifically an avipoxvirus and even more specifically FPV. Those recombinant live vectors are used to induce a TH1 immune response and cytotoxic T cells against HIV in animals or humans.

Even more specifically this invention relates to FPV recombinant for those chimeric proteins and particularly to the recombinant FPV strains denominated FPCR3 and FPSCR3gpt, which contains the chimeric gene cr3. Once assembled as described above cr3 is cloned in a poxvirus recombination vector, in particular a FPV recombination vector. In this particular case plasmids pEFL29 y pFP67xgpt were used as recombination vectors. pEFL29 presents homologous regions to the 6 kb BamHI terminal fragment of FPB genome, which flanks the transcriptional unit in which the heterologous gene is inserted under the control of VV 7.5K promoter, and contains also the reported gene y lacZ under the control of 4b promoter of FPV. pFP67xgpt employs open reading frames 6 and 7 from the 11.2 kb BamHI region as homologous recombination signals. Those regions flanks the transcriptional unit in which the heterologous gene is place under the synthetic poxviral E/L promoter and it also contains the gpt gene which confers resistance to mycophenolic acid which allows the selection of recombinant viruses.

The resultant plasmids were denominated pFPCR3 y pFPSCR3gpt respectively. Those plasmids are transfected in a primary culture of Chicken Embryo Fibroblasts (CEF) using one of the several transfection techniques available in the state of the art. In this particular case the transfection is carried out using lipofectin (Sigma, USA) in CEF previously infected with the FP29 strain of FPV but other methods such as electroporation and DEAE Dextran, among others, can be used. As a result of the homologous recombination between plasmid and the corresponding non-essential regions on the FPV genome recombinant viruses, which expressed B galactosidase, can be recovered in the case of pFPCR3 or resistant to mycophenolic acid in the case of pFPSCR3gpt. The presence of the selection marker allows the identification of recombinant viral plaques and their purification by several passages on CEF. The presence of the heterologous gene on the selected viruses can be verified by PCR and the expression of the protein can be verified by western blot.

This invention relates also to the use of recombinant FPV, obtained as described, to induce a TH1 immune response with CTL activity in Balb/c mice alone or in combination with a pharmaceutically accepted formulation selected from those in the state of the art.

This invention refers also to a therapeutic or preventive combination of recombinant FPV for the described chimeric genes, and particularly to FPCR3 and FPSCR3gpt, with immunomodulators or adjuvants in particular with cytokines such as IL2, IL12, IFNγ, GMSCF, GSCF, among others, which stimulates preferentially the TH1 immune response.

Particularly it refers to combination of viruses FPCR3 or FPSCR3gpt with daily doses of IL2 in a range between $10^2$ y $10^7$ iu in animals or humans. The daily administration of IL2 to Balb/c mice starting the day of the administration of the FPV or after potentiates the cellular immune response against CR3.

Although it refers particularly to CR3, it is in the essence of this invention that CTL rich fragments other than those in CR3 or fragments equivalent to those in CR3 but from other HIV-1 isolates can also be used.

Similarly, although it refers particularly to FP9 strain of FPV, it is in the essence of this invention that other FPV parental strains can be used to construct the recombinant viruses, as well as another avipoxvirus such as CPV, other poxvirus such as VV or MVA or still other viruses such as herpesvirus, alphavirus, adenovirus, poliovirus or even bacterias such as BCG or *Salmonella*.

In another embodiment of the present invention the gene can be cloned in a proper plasmid vector for expression in mammalian cells and be injected into a mammal to induce a TH1 immune response and CTL activity in combination with a pharmaceutically acceptable carrier.

In still another embodiment of the invention it is also included a therapeutic or preventive combination of those recombinant plasmids described above with immunomodulators or adjuvants such as described or still others such as liposomes, polysaccharides, lipopeptides, lipids, proteoliposomes or combinations thereof.

In still another embodiment of this invention those genes can be clones in other plasmids for expression of the recombinant proteins in bacteria, yeast, fungi, insect or mammalian cells, plants or in the milk of transgenic animals. The proteins recovered from these systems could also be used to induce a TH1 immune response and CTL activity in animals or humans when administered in an appropriate expressed in a pharmaceutically acceptable carrier.

In still another embodiment of the invention, therapeutic or preventive combinations of CR3 protein with immunomodulators or adjuvants such as described above or still others such as liposomes, polysaccharides, lipids, proteoliposomes or other adjuvants available according to the state of the art capable to potentiate the TH1 type immune response and CTL activity in animals or humans.

EXAMPLES

Example 1

Figure 1:
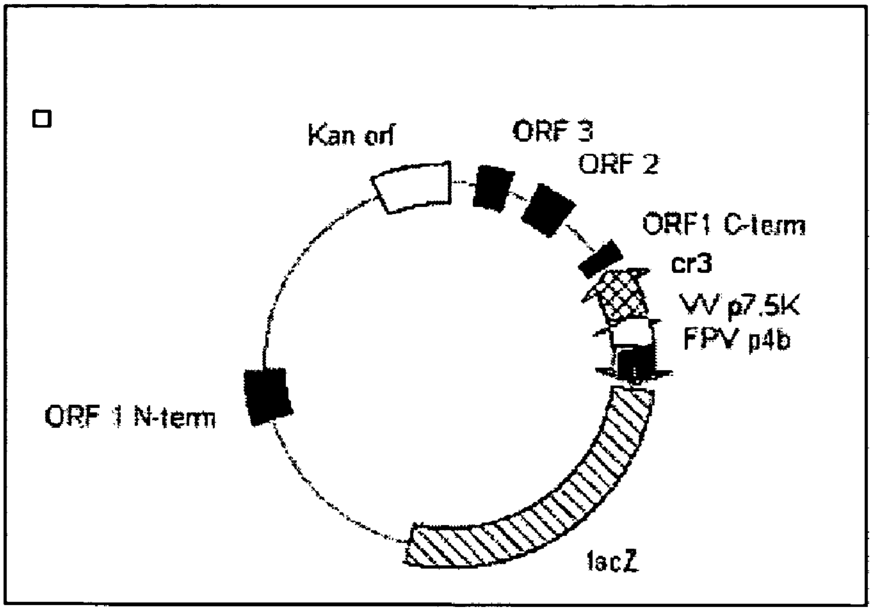
FIG. 1. Plasmid pEFL-cr3, for the homologous recombination in Fowlpox using the ORF-1 from the BamH16 Kb terminal region as insertion site. The gene cr3 is under the control of VV p7.5K promoter and the reporter gene LacZ under FPV 4b promoter.
Figure 2:
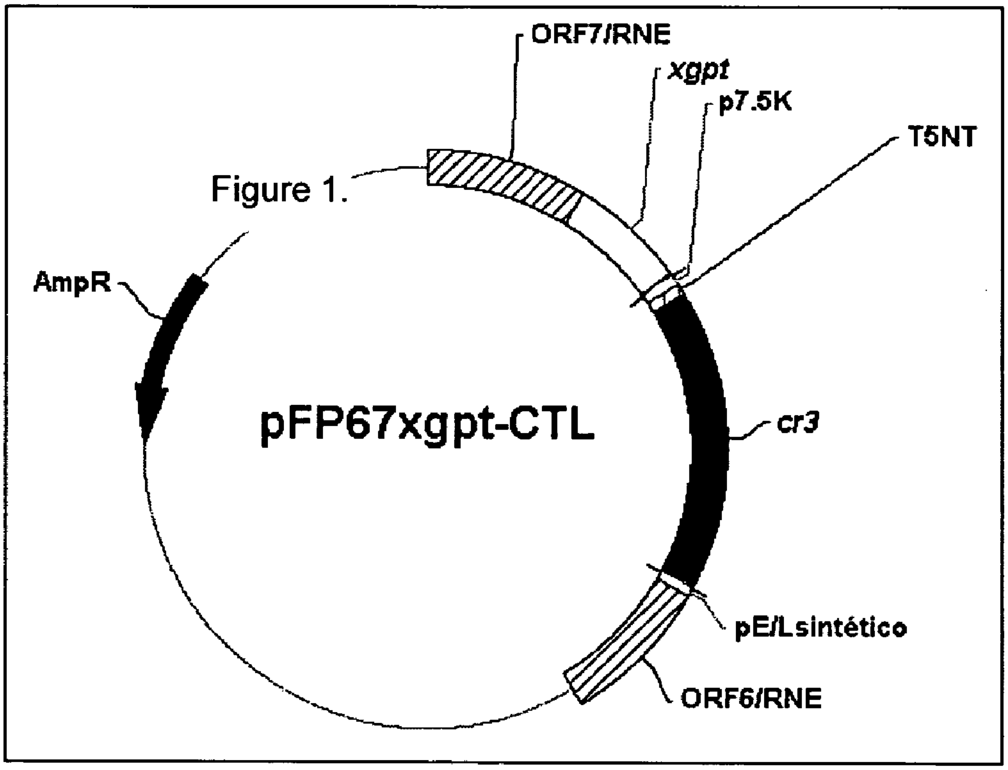
FIG. 2. Plasmid pFP67xgpt, for homologous recombination in FPV using the DNA region between ORF-6 and ORF-7 from the 11.2 kb BamHI fragment as insertion site. The gene cr3 is placed under the control of the synthetic promoter E/L and the gene Ecogpt under the control of W 7.5K promoter.

Obtention of cr3 cr3 (SEQ. ID. NO:1) is a chimeric gene assembled by fragments of different HIV genes. It was assembled on pTAB11 plasmid, which is essentially equal to pTAB9 (Gómez C E, Navea L, Lobaina L, Dubed M, Expósito N, Soto A and Duarte C A. The V3 loop based Multi-Epitope Polypeptide TAB9 Adjuvated with Montanide ISA720 is Highly Immunogenic in Nonhuman Primates and Induces Neutralizing Antibodies Against Five HIV-1 isolates. Vaccine 17:2311-2319, 1999), but has the T1 and T2 T helper cell epitopes from gp120 at the 5' end extreme of the gene instead of the fragment codifying encoding for the N-terminal part of the P64K protein. A 186 bp blunt-BamHI synthetic DNA fragment encoding for the T2 epitope from gp120, the V3 epitope of the MN strain, and T helper cell epitopes from gp41 and vpr, was cloned intoEcoRV-BamHI cut pTAB11 previously digested EcoRV-BamHI. DNA sequences encoding for two consecutive lysines were inserted between individual epitopes to facilitate intracellular processing. The resultant plasmid was named pCR1. A 603 bp fragment encoding codifying for the p66/p51 (RT) protein (pos. 2663-3109 from HIV-1 SF2 provirus) was PCR amplified using the O.2660 and O.2661 primers (table 1). The PCR fragment was extracted from low-melting agarose following a digestedion BglII-EcoRI and subcloned into the BglII-EcoRI cut pCR1 vector to obtain the pCR2 plasmid encoding codifying for CR2 protein. Next, a 324 bp fragment, comprising a sequence of the nef gene (pos. 8516-8818 from HIV-1 LAI isolate), was PCR amplified with primers O.2662 and O.2663 primers. Finally, another segment of 267 bp in the gag gene p24 coding region (pos. 1451-1696 from HIV-1 SF2) was amplified using primers O.2664 and O.2665 (table 1) primers. Then, an overlapping PCR was accomplished using 20 pmol of primers O.2662 and O.2666 (table 1) primers. Equal amount of each band (0.47 pmol) were mixed in PCR buffer [KCl 50 mM; Tris-HCl 10 mM, (pH 8.3), at 25° C.; gelatin 0.001%], $MgCl_2$2.5 mM, dNTP 0.2 mM each and 4 U of Taq Polymerase, in a volume of 50 μL. To promote the annealing of the bands by the complementary 9 bp ends of O.2663 and O. 2664 oligonucleotides, the mixture was first heated atto 92° C. for 2 min and then cooleding atto 50° C. Finallyto get the extention from the annelated segments, the temperature was increased to 72° C. during 5 min to extend the annealed segments. Afterward, 10 μL of the above reaction was added to a mixture of PCR Buffer containing 2.5 mM $MgCl_2$, 0.2 mM dNTPs, 20 pmol of O.2662 and 20 pmol of O.2666 and 4 U Vent pol. in 50 μL as total volume. Standard amplification conditions were 92° C. for 2 min, followed by 30 cycles of 92° C. for 40 sec, 50° C. for 1 min and 72° C. for 1 min, and a final extention extension at 72° C. for 5 min. Next, the overlapping nef-p24 amplified band was purified from electrophoresis in low-melting agarose and digested with XbaI. Finally, the former blunt-XbaI band was cloned into a NruI-XbaI cut pCR2 vector previously cut NruI-XbaI to obtain pCR3 plasmid. cr3 encodes therefore for a chimeric proteins which includes T helper cells and CTL epitopes from gp120, gp41, vpr, RT, nef and gag presented by a wide range of HLA antigens (table 2).

TABLE 1

DNA SEQUENCE OF OLIGONUCLEOTIDES USED IN PCR REACTIONS

| Oligonucleotide | Sequence (5'-3') |
|---|---|
| 0.2660 | GAAGATCTGTACAGAAATGGAAAAG (SEQ. ID. NO:2) |
| 0.2661 | GGAATTCTCGCGATCCTACATACAAATCATC (SEQ. ID. NO:3) |
| 0.2662 | GACATCACAAGTAGCAATACAGC (SEQ. ID. NO:4) |

TABLE 1-continued

DNA SEQUENCE OF OLIGONUCLEOTIDES USED IN PCR REACTIONS

| Oligonucleotide | Sequence (5'-3') |
|---|---|
| 0.2663 | CCCTGCATGTGGCTCAACTGGTACTAGCTTG (SEQ. ID. NO:5) |
| 0.2664 | GTTGAGCCACATGCAGGGCCTATTGCAC (SEQ. ID. NO:6) |
| 0.2665 | GCTCTAGATTATTCGGCTCTTAGAGTTTTATAG (SEQ. ID. NO:7) |
| 0.2666 | GCTCTAGATTATTCGGCTCTTAGAG (SEQ. ID. NO:8) |

TABLE 2

T CELL EPITOPES IN CR3

| | Epit p s | HLAI | HLAII |
|---|---|---|---|
| p24 87-175 | | | |
| 87-101 | HAGPIAPGQMREPRG (SEQ. ID. NO:14) | A2 | |
| 91-110 | IAPGQMREPRGSDIAGTTST (SEQ. ID. NO:15) | A2, A24, B13, B38 | |
| 101-120 | GSDIAGTTSTLQEQIGWMTN (SEQ. ID. NO:16) | A26, A30, B38 | |
| 108-117 | TSTLQEQIGW (SEQ. ID. NO:17) | B*5701, B*57, B*5801, B57, B58 | |
| 121-135 | NPPIPVGEIYKRWII (SEQ. ID. NO:18) | B8 | |
| 121-142 | NPPIPVGEIYKRWIILGLNKIV (SEQ. ID. NO:19) | B8, B27, A33, B35 | |
| 122-130 | PPIPVGEIY (SEQ. ID. NO:20) | B*3501 | |
| 124-138 | IPVGEIYKRWIILGL (SEQ. ID. NO:21) | B8 | |
| 127-135 | GEIYKRWII (SEQ. ID. NO:22) | B8 | |
| 128-136 | EIYKRWIIL (SEQ. ID. NO:23) | B8, B*0801 | |
| 129-138 | IYKRWIILGL (SEQ. ID. NO:24) | A*2402 | |
| 130-148 | YKRWIILGLNKTVRMYSPT (SEQ. ID. NO:25) | B27 | |
| 1301-139 | KRWIILGLN (SEQ. ID. NO:26) | B27 | |
| 134-143 | IILGLNKIVR (SEQ. ID. NO:27) | A33 | |
| 136-145 | LGLNKIVRMY (SEQ. ID. NO:28) | Bw62 | |
| 136-146 | LGLNKIVRMYS (SEQ. ID. NO:29) | B62 | |
| 137-145 | GLNKIVRMY (SEQ. ID. NO:30) | B*1501, B62 | |
| 151-170 | LDIRQGPKEPRDYVDRFYK (SEQ. ID. NO:31) | ND | |
| 162-172 | RDYVDRFYKTL (SEQ. ID. NO:32) | (B44, or A26, or B70), B*4402, A*2402 | |
| 166-174 | DRFYKTLRA (SEQ. ID. NO:33) | B*1402, B14 | |
| Nef 43-150 | | | |
| 68-76 | FPVTPQVPL (SEQ. ID. NO:34) | B*3501, B35, B7 | |

TABLE 2-continued

T CELL EPITOPES IN CR3

| | Epit p s | HLAI | HLAII |
|---|---|---|---|
| 68-77 | FPVTPQVPLR (SEQ. ID. NO:35) | B7, B*0702 | |
| 71-79 | TPQVPLRPM (SEQ. ID. NO:36) | B*0702 | |
| 74-81 | VPLRPMTY (SEQ. ID. NO:37) | B35 | |
| 73-82 | QVPLRPMTYK (SEQ. ID. NO:38) | A3; A11; B35 | |
| 74-81 | VPLRPMTY (SEQ. ID. NO:39) | B35, B*3501 | |
| 75-82 | PLRPMTYK (SEQ. ID. NO:40) | A*1101 | |
| 82-91 | KAAVDLSHFL (SEQ. ID. NO:41) | Cw8, C*0802 | |
| 83-94 | AAVDLSHFLKEK (SEQ. ID. NO:42) | A11 | |
| 84-91 | AVDLSHFL (SEQ. ID. NO:43) | Bw62 | |
| 84-92 | AVDLSHFLK (SEQ. ID. NO:44) | A11, A*1101 | |
| 86-94 | DLSHFLKEK (SEQ. ID. NO:45) | A3.1 | |
| 86-100 | DLSHFLKEKGGLEGL (SEQ. ID. NO:46) | A2, B35, C4 | |
| 90-97 | FLKEKGGL (SEQ. ID. NO:47) | B8 | |
| 92-100 | KEKGGLEGL (SEQ. ID. NO:48) | B60, B*4001 | |
| 93-106 | EKGGLEGLIHSQRR (SEQ. ID. NO:49) | A1, B8 | |
| 102-115 | HSQRRQDILDLWIY (SEQ. ID. NO:50) | B7 | |
| 103-127 | SQRRQDILDLWIYHTQGYFPDWQNY (SEQ. ID. NO:51) | B13 | |
| 105-114 | RRQDILDLWI (SEQ. ID. NO:52) | B*2305 | |
| 106-115 | RQDILDLWIY (SEQ. ID. NO:53) | B27 | |
| 115-125 | YHTQGYFPDWQ (SEQ. ID. NO:54) | B17 | |
| 116-125 | HTQGYFPDWQ (SEQ. ID. NO:55) | B57 | |
| 117-128 | TQGYFPDWQNYT (SEQ. ID. NO:56) | B17; B37 | |
| 117-127 | TQGYFPDWQNY (SEQ. ID. NO:57) | Bw62, B*1501 | |
| 120-128 | YFPDWQNYT (SEQ. ID. NO:58) | B*3701, B*5701, B15, B37, B57 | |
| 120-144 | YFPDWQNYTPGPGIRYPLTFGWCYK (SEQ. ID. NO:59) | A24 | |
| 126-137 | NYTPGPGVRYPLT (SEQ. ID. NO:60) | B7 | |
| 128-137 | TPGPGVRYPLT (SEQ. ID. NO:61) | B*0702, B*4201, B7, B7(*8101) | |
| 130-143 | GPGVRYPLTFGWCY (SEQ. ID. NO:62) | B*57 | |
| 132-147 | GVRYPLTFGWCYKLVP (SEQ. ID. NO:63) | B18, A1, B8 | |
| 133-148 | VRYPLTFGWCYKLVPV (SEQ. ID. NO:64) | B57 | |
| 135-143 | YPLTFGWCY (SEQ. ID. NO:65) | B*1801, B18, B35, B49 | |
| 136-145 | PLTFGWCYKL (SEQ. ID. NO:66) | A*0201, A2 | |
| RT 36-192 | | | |
| 36-52 | EICTEMEKEGKISKIGP (SEQ. ID. NO:67) | ND | |
| 42-50 | EKEGKISKI (SEQ. ID. NO:68) | B*5101, B51 | |
| 93-101 | GIPHPAGLK (SEQ. ID. NO:69) | A3 | |
| 98-113 | AGLKKKKSVTVLDVGD (SEQ. ID. NO:70) | Cw4 | |

TABLE 2-continued

| | T CELL EPITOPES IN CR3 | | |
|---|---|---|---|
| | Epit p s | HLAI | HLAII |
| 103-107 | KKSVTVLDVGDAYFS (SEQ. ID. NO:71) | Cw4 | |
| 107-115 | TVLDVGDAY (SEQ. ID. NO:72) | B35, B*3501 | |
| 108-118 | VLDVGDAYFSV (SEQ. ID. NO:73) | A*0201, A2 | |
| 113-120 | DAYFSVPL (SEQ. ID. NO:74) | B*5101, B24 | |
| 118-127 | VPLDEDFRKY (SEQ. ID. NO:75) | B35, B*3501 | |
| 126-135 | KYTAFTIPSI (SEQ. ID. NO:76) | A2 | |
| 128-135 | TAFTIPSI (SEQ. ID. NO:77) | B51, B*5101 | |
| 151-159 | QGWKGSPAI (SEQ. ID. NO:78) | B*5101 | |
| 153-165 | WKGSPAIFQSSMT (SEQ. ID. NO:79) | B27 | |
| 156-164 | SPAIFQSSM (SEQ. ID. NO:80) | B7, B35, B*3501 | |
| 158-166 | AIFQSSMTK (SEQ. ID. NO:81) | A*0301, A*1101, A3, A*6801, A11, A3.1, B*0301 | |
| 175-142 | KQNPDIVIY (SEQ. ID. NO:82) | A*3002 | |
| 177-185 | NPDIVIYQY (SEQ. ID. NO:83) | B35, B*3501 | |
| 181-189 | VIYQYMDDL (SEQ. ID. NO:84) | A2, A*0201 | |
| 181-191 | VIYQYMDDLYV (SEQ. ID. NO:85) | A*0201 | |
| 172-192 | FRKQNPDIVIYQYMDDLYVG (SEQ. ID. NO:86) | | DR1, 2 ó 3, 4, 7 |
| T1-T2 gp120 | | | |
| 421-440 | KQIINMWQEVGKAMYAPPIE (SEQ. ID. NO:87) | A2 | several |
| 436-442 | KVGKAMY (SEQ. ID. NO:88) | A2 | |
| 436-443 | KVGKAMYA (SEQ. ID. NO:89) | A2 | |
| 105-117 | HEDIISLWNQSLK (SEQ. ID. NO:90) | A2 | several |
| 115-123 | IISLWNQSL (SEQ. ID. NO:91) | A2.1 | |
| gp 41 | | | |
| 584-594 | ERYLKDQQLLG (SEQ. ID. NO:92) | B14; B8; A24 | |
| 582-593 | YLKDQQLL (SEQ. ID. NO:93) | B8, B*0801, A*2402 | |
| 580-593 | ERYLKDQQLL (SEQ. ID. NO:94) | A*2402, B*0801, B8 | |
| 581-592 | RYLKDQQL (SEQ. ID. NO:95) | B14, B*1402 | |
| Vpr | | | |
| 66-80 | QLLFIHFRIGCRHSR (SEQ. ID. NO:96) | | ND |

Numbers represent positions relative to the HXB2 amino acid sequence of each viral protein, the viral isolate is within parenthesis; ND, not defined.

Example 2

Cloning of cr3 in pFPL29

In pCR3, the cr3 gene was cloned under the control of pTryp, with a ClaI site on the 5' and the T4 phage gene 32 terminator and a HindIII site at 3'. This plasmid was digested ClaI and HindIII, and treated with Klenow I to obtain a cr3 gene with ATG at the 5' end and translation stop codons at 3'. This DNA fragment was cloned in the poxvirus recombination vector pEFL29.

pEFL29 has the BamH1 6 Kb terminal fragment of FPV as non-essential regions for homologous recombination in the FPV genome. This fragment contains three ORF and the ORF1 is interrupted. Flanked by these homology regions are the VV p7.5K, promoter, followed by a SmaI site and the reporter gene lacZ under the control of the late promoter 4b of FPV. This plasmid includes also the kanamycin resistance gene and a bacterial origin of replication.

PEFL29 was SmaI digested, treated with alkaline phosphatase and ligated with a ClaI/HindIII digested band containing cr3 gene. Several clones with cr3 in the right orientation under the p7.5K were selected. *E. coli* strain DH5α (φ80dlacZΔM15, recA1, endA1, gyrA96, thi-1, hsdR17 (rK−mK+), supE44, relA1, deoR, Δ(lacZYA-argF) U169) was used for propagation and selection of recombinant plasmids in LB medium containing kanamicin (25 μg/ml). All genetic manipulations were made according to Sambrook y col (Sambrook J, Fritsh E F, Maniatis T. 1989. Molecular Cloning. A Laboratory Manual. Sec Ed. Cold Spring Harbor Laboratory, Cold Spring Harbor, N.Y.)

The DNA sequenced of clone pEFL-cr3 (FIG. 1), was verified using an automatic sequence processor (Pharmacia). This clone was purified using CsCl gradient and used to transfect chicken embryo fibroblasts (CEF).

Example 3

Cloning cr3 in pFP67xgpt cr3 gene was PCR amplified and cloned in pMosblue vector (Amersham, UK). The resultant plasmid was named pTCR3. pTCR3 was HpaI/BamHI digested and the shorter band containing cr3 was cloned in the poxvirus vector pFP67xgpt.

pFP67xgpt has a fragment of the 11.2 Kb BamH1 of FPV genome as non-essential region for homologous recombination in the FPV genome (Tomley F, Binns M, Campwell J, Boursnell M. Sequence Analysis of an 11.2 Kilobase, near-terminal, Bam HI fragment of fowlpox virus, J Gen Virol, 1988, 69, 1025-1040). This fragment contains the open reading frame 6 and 7 of this region and the insertion occurs at the intergenic region. Flanked by these homologous regions are an E/L synthetic promoter (Carroll M W, Moss B. *E. coli* B-glucoronidase (GUS) as a marker for recombinant vaccinia viruses, Biotechniques, 1995, 19, 3: 352-354), and the reporter gene Ecogpt under the control of 7.5K promoter of VV. This plasmid includes also the kanamycin resistance gene and a bacterial origin of replication.

Plasmid pFP67xgp was cut StuI/BamHI and ligated with a cr3 containing DNA fragment derived from the HpaI/BamHI digestion of pTCR3. Several clones with cr3 in the proper orientation under the E/L synthetic promoter were selected (FIG. 1). *E. coli* strain DH5α (φ80dlacZΔM15, recA1, endA1, gyrA96, thi-1, hsdR17 (rK−mK+), supE44, relA1, deoR, Δ(lacZYA-argF)U169) was used for propagation and selection of recombinant plasmids in LB medium containing ampicillin (50 μg/ml). All genetic manipulations were made according to Sambrook et al. The DNA sequenced of clone pFP67xgptct was verified using an automatic sequence processor (Pharmacia). This clone was purified using CsCl gradient and used to transfect CEF).

Example 4

Generation of Recombinant FPVs

The parental FPV used for the generation of recombinants was the attenuated HP-438 strain, which was derived from the pathogenic strain HP-1 by six consecutive passages on CEFs, two further passages on chorioallantoic membranes, and finally 438 passages through CEFs (Mayr A and K Malicki. 1966. Attenuierung von virulentem Huhnerpockenvirus in Zellkulturen und Eigenschaften des attenuierten Virus. Zentralbl. Veterinaermed. Reihe B 13: 1-13). A twice-plaque-purified isolate of HP438 (FP9) was then passaged six times to constitute a stock. FPV stocks were grown on CEFs in 199 medium containing 2% newborn calf serum (NBCS).

Recombinant FPV were generated by homologous recombination between FP9 and plasmid pEFL29 or its derivatives as previously described. CEFs grown in 25 cm2 flasks were infected with FP9 at a multiplicity of infection (m.o.i) of 2 plaque forming units (pfu)/cell, then 2 hours later the cells were transfected with CsCl purified 10 μg of plasmid DNA (pEFL-cr3 or pFP67xgptctl) using 20 μg of Lipofectin (Gibco BRL, USA). Fresh medium (3 ml of 199 medium containing 10% tryptose phosphate broth plus 2% NBCS) was added and the cells were incubated at 37° C. in a $CO_2$ incubator. Fresh medium was added again after 24 h, and then the cells were incubated for a further 3 to 4 days. After that time, the cells were freeze-thawed three times. The cell lysate was then titrated in CEF to select the recombinant viruses. After 2 hrs of adsorption the viral inoculum was removed and a layer of agarose containing EMEN was added. This layer was prepared by mixing identical volumes of 2% low melting agarose and EMEN 2×. (Gibco, Grand Island, N.Y.) with 4% fetal calf serum (Gibco, Grand Island, N.Y.). At day four viral plaques were evident. CEFs transfected with pEFL-cr3 were stained by adding another agarose layer with 0.33% Xgal (Melford Laboratories, UK) to the cultures. Blue plaques were selected and purified three times until 100% of viral plaques were positive for B galactosidase expression. Stocks of lacZ+viruses were then amplified in CEF grown in 25 cm2 flasks in 199 medium containing 10% tryptose phosphate broth plus 2% NBCS. The selected recombinant FPV was named FPCR3.

Selective medium for transfection with plasmid pFP67xgptctl contained mycophenolic acid (25 μg/ml), xantine (250 μg/ml) and hypoxantine (1 μg/ml). At day four viral plaques were evident. Since gpt and cr3 genes are flanked by the same homology regions the isolation of viral plaques in selective medium indicate that recombination occurred and both genes are inserted in FPV genome. Plaques were purified three consecutive times in CEF. The recombinant virus selected was named FPSCR3GPT.

Example 5

PCR Analysis of FPCR3

PCR analysis was used to check that the FPCR3 recombinants contained the cr3 gene. Recombinant FPV were propagated in CEFs for 6 days and then the cells were harvested and pelleted. The pellet was suspended and incubated for 2 h at 55° C. in 200 μl of extraction buffer (10 mM Tris HCl, 100 mM NaCl, 10 mM EDTA, 0.5% SDS, 2% β-mercaptoethanol) containing 1.25 mg/mi of proteinase K. The DNA was then phenol-chloroform extracted and ethanol precipitated. DNA from each virus was tested by PCR with the primers described below, complementary to sequences in the 5' and 3' of cr3 gene, respectively. The PCR conditions used were 5 min at 94° C. followed by 25 cycles of 1 min at 94° C., 1 min 30 sec at 45° C. and 1 min 30 sec at 72° C. and a final extension at 72° C. for 10 min. The primer sequences were as follows:

```
primer 775,    5' TATTAACATTGCCTAGTAG 3'
               (SEQ. ID. NO:9)

primer 776,    5' GAAGTAGAATCATAAAGAAC 3'
               (SEQ. ID. NO:10)
```

Figure 3:
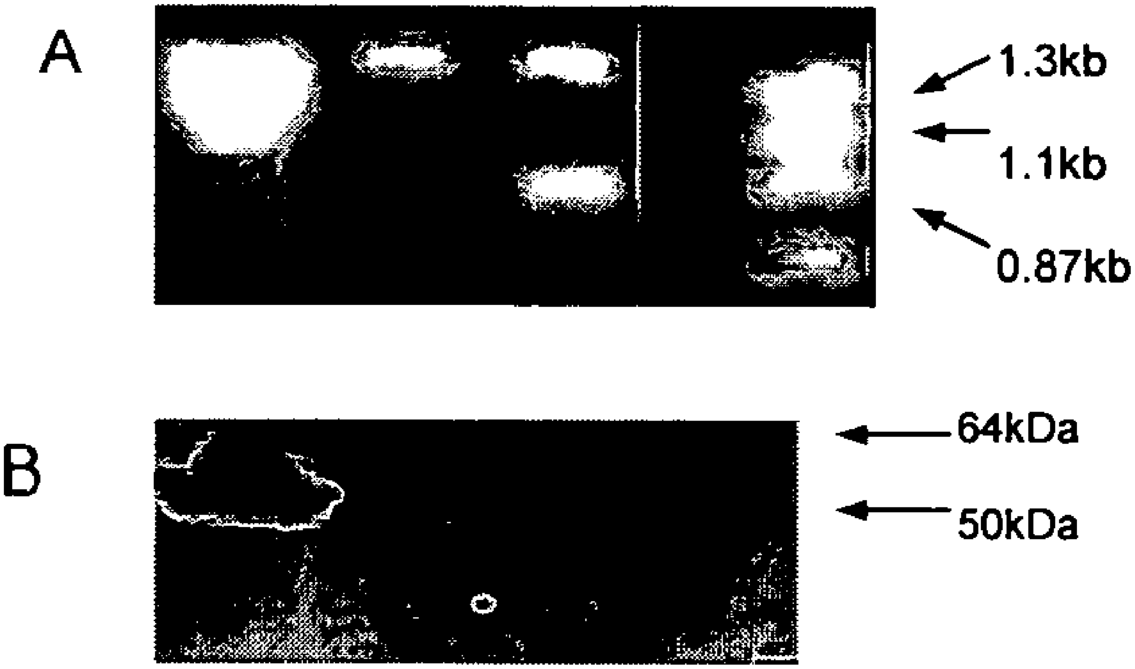
FIG. 3. (A) PCR and (B) Western blot of three independent cr3 recombinant FPVs: (1) FPCR3.1; (2) FPCR3.2; (3) FPCR3.3; (4) FPL29; (5) DNA molecular weight marker.

Three independent CR3 recombinant viruses (FPCR3.1; FPCR3.2; FPCR3.3), showed the expected 1.3 kb band after the PCR reaction. This band was absent for the parental virus FPL29 (FIG. 3A).

Example 6

PCR Analysis FPSCR3GPT

PCR analysis was used to check that the FPSCR3GPT recombinants contained the cr3 gene. Recombinant FPV were propagated in CEFs for 6 days, and then the cells were harvested and pelleted. The pellet was suspended and incubated for 2 h at 55° C. in 200 μl of extraction buffer (10 mM Tris HCl, 100 mM NaCl, 10 mM EDTA, 0.5% SDS, 2% β-mercaptoethanol) containing 1.25 mg/ml of proteinase K. The DNA was then phenol-chloroform extracted and ethanol precipitated. DNA from each virus was tested by PCR with the primers described below, complementary to sequences in the 5' and 3' of cr3 gene, respectively. The PCR conditions used were 5 min at 94° C., followed by 25 cycles of 1 min at 94° C., 1 min 30 sec at 45° C., and 1 min 30 sec at 72° C., and a final extension at 72° C. for 10 min. The primer sequences were as follows:

```
primer 2660,  5' GAAGATCTGTACAGAAATGGAAAAG 3'
 (257-279)    (SEQ. ID. NO:11)

primer 2663,  5' CCCTGCATGTGGCTCAACTGGTACTAGCTTG 3'
(1029-1059)   (SEQ. ID. NO:12)
```

Figure 4:
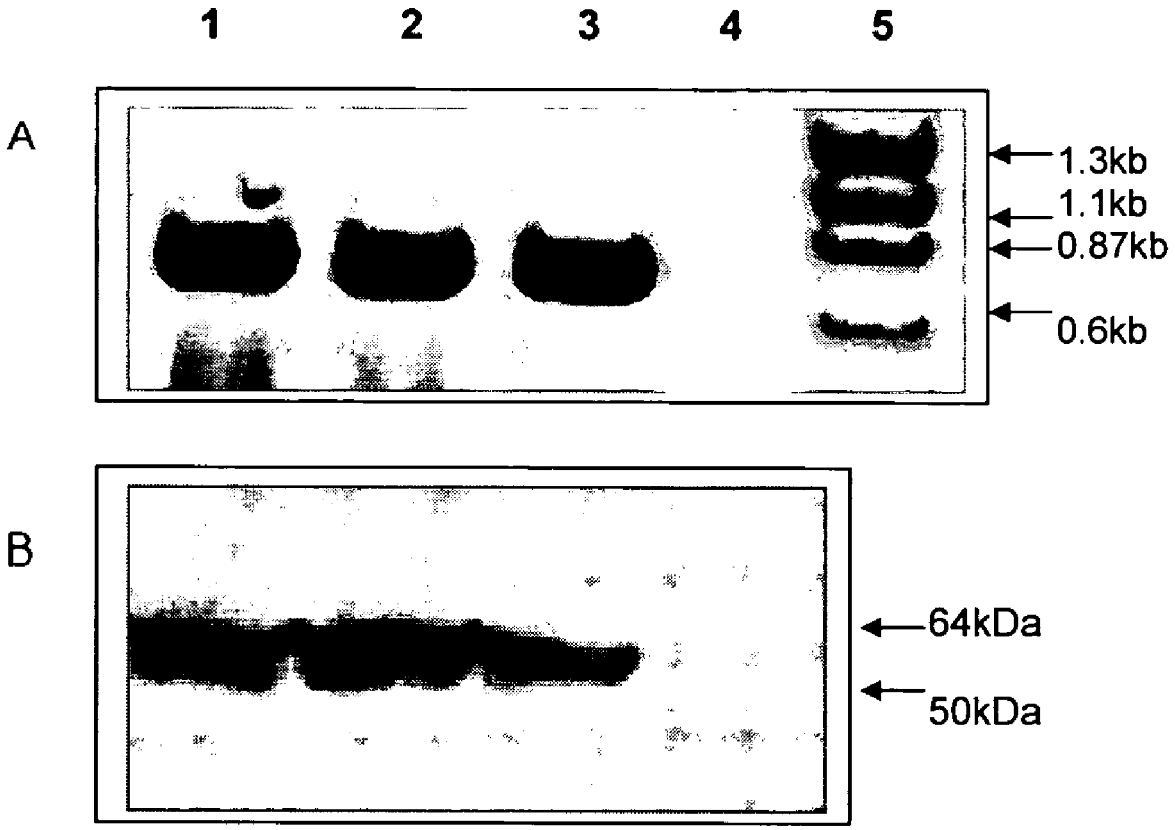
FIG. 4. (A) PCR with cr3 internal oligonucleotides (B) Western blot from three independent cr3 recombinant FPV (1) FPSCR3GPT.1; (2) FPSCR3GPT.2; (3) FPSCR3GPT.3; (4) parental virus; (5) Molecular weight marker.

Three independent recombinant viruses (FPSCR3gpt.1; FPSCR3gpt.2; FPSCR3gpt.3), showed the expected 800 pb band after the PCR reaction. This band was absence for the parental virus FPL29 (FIG. 4A).

Example 7

Evaluation of CR3 Expression by CEF Infected by FPCR3

Expression of CR3 by the FPCR3 was confirmed by Western blotting. Confluent CEFs in 60 mm Petri dishes were infected at 0.5 pfu/cell with recombinant FPV. After 24 hours the cells were harvested, pelleted and suspended in 1×SDS gel-loading buffer (50 mM Tris HCl pH 6.8, 100 mM DTT, 2% SDS, 0.1% bromophenol blue, 10% glycerol). Proteins were fractionated by sodium dodecyl sulphate-polyacrylamide gel electrophoresis (SDS-PAGE) on a 15% gel. They were then electro-transferred onto a nitrocellulose membrane (Hybond-C, Amersham, UK) following standard protocols. After transfer, the membrane was blocked overnight in 5% non-fat dry milk in phosphate buffered saline (PBS: 2.68 mM KCl, 1.47 mM KH2PO4, 0.137M NaCl, 8.06 mM Na2HPO4). It was then incubated for 2 h at room temperature with 10 ug/ml of monoclonal antibody 6.2, diluted in PBS containing 1% dried milk. This monoclonal antibody was produced in mice immunized with CR3 (Iglesias E, Ruiz M, Carrazana Y, Cruz L J, Aguilar A, Jiménez V, Carpio E, Martíenez M, Pérez M. Martínez C, Cruz O, Martín A, Duarte C. Chimeric proteins containing HIV-1 epitopes. Journal Biochemistry, Molecular Biology and Biophysics, 2001, 5: 109-20.). The membrane was then washed and incubated with a sheep anti-mouse antibody (1:2000) conjugated to horseradish peroxidase (HRPO) (Amersham, UK). After several washes, the immunoblots were developed using the ECL Western blot detection system (Amersham, UK) according to the manufacturers' instructions. A specific band with a molecular weight between 50 y 64 kDa was detected in FPCR3 infected cultures. No protein was detected in CEF infected with the parental FP9 virus (FIG. 3B)

Example 8

Evaluation of CR3 Expression by CEF Infected by FPSCR3gpt

Expression of CR3 by the FPSCR3gpt was confirmed by Western blotting following a procedure similar to the one described in the previous example. A specific band with a molecular weight between 50 y 64 kDa was also detected in FPSCR3gpt infected cultures while no protein was detected in CEF infected with the parental FP9 virus (FIG. 4B).

Example 9

Purification of FPCR3 and FPSCR3gpt and Immunization of Mice

Figure 5:
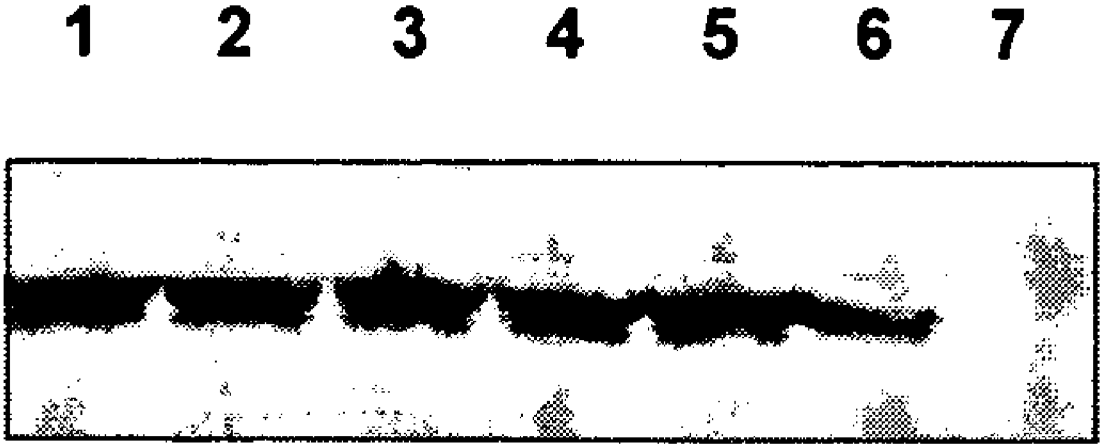
FIG. 5. Stability of CR3 expression assessed by Western blot. Lanes represent three independent samples of FPV infected with FPSCR3GPT from the viral stock (1,2,3) or purified by sucrose cushion (4,5,6). Lane 7 represents CEF infected with the parental virus.

Large stocks of recombinant FPV were grown on CEFs obtained from eggs of a specific pathogen-free flock. FPV was purified by centrifugation of cytoplasmic extracts through a 25% (w/v) sucrose cushion in a Beckman SW28 rotor at 29000 rpm for 2 hours. Virus titers were then determined by plaque assay on CEF monolayers. FIG. 5 shows that CR3 expression did not varies after scaling up of the culture.

Young adult (five to eight-week-old) female Balb/c mice (obtained from the SPF breeding colony at the Institute for Animal Health, Compton, UK, or the Centro Nacional de Producción de Animales de Laboratorio (CENPALAB), Cuba) were primed by the intravenous (i.v), intraperitoneal (i.p), or subcutaneous (s.c) routes with 2.5-5×$10^7$ pfu of FPCR3, FPSCR3gpt or the negative control virus in 200 μl sterile PBS. Two to four weeks later, mice were boosted by the same route with a second dose of 2.5-9×$10^7$ pfu of the same viruses in 200 μl sterile PBS.

Example 10

Detection of CTL Response Against CR3 in Balb/c Mice

Enzyme-linked-immunospot (ELISPOT) assays for detection of antigen-specific IFN-γ-releasing cells were performed using a method based on that previously described (Tanguay S and J J Killion. Direct comparison of ELISPOT and ELISA-based assays for detection of individual cytokine-secreting cells. 1994. Lymphokine Cytokine Res, 13: 259-263). Briefly, immobilon-P membrane 96-well plates (Millipore, Molsheim, France) were coated with 100 μl/well of 5 μg/ml murine IFN-γ specific monoclonal antibody R4 (Pharmingen, San Diego, Calif.) overnight at 4° C., washed 3× with PBS and blocked using RPMI 1640 medium supplemented with 10% FBS at 37° C. for 1 h. Test cells were then added: these were either ex vivo splenocyte suspensions (prepared as described above) from mice primed and boosted with FPCR3 or FPSCR3gpt. Different numbers of test cells were added per well: $10^6$, 2×$10^5$ and 4×$10^4$. Cells were stimulated by addition of P815 cells incubated with synthetic peptides at 1 μM or infected with VV recombinant for CR3, Gag, or Nef at a m.o.i of 5 pfu/cell. P815 cells without peptide or infected with control vaccinia viruses (vSC8 or wild type vaccinia strain WR) were included to reveal background numbers of IFN-γ-producing cells. Each well had a final volume of 200 μl of R10 medium plus hIL-2. All assay variables were tested in duplicate. After incubation overnight (at least 17 hours), the plates were washed 3× with PBS and 5× with PBS plus 0.05% Tween 20, then a secondary biotin-conjugated antibody XMG1.2 (Pharmingen, San Diego, Calif.) was added at 0.5 μg/ml and reacted at room temperature for 2 h. The wells were washed 5× with PBS plus 0.05% Tween 20, and alkaline phosphatase (AP)-labeled streptavidin (Vector Labs, CA, USA) was added at a 1/1000 dilution in PBS plus 0.05% Tween 20 for 1 h at room temperature. The wells were washed again 3× with PBS plus 0.05% Tween 20 and 3× with PBS, and the spots were developed using an AP activity kit (Biorad, CA, USA). After 15 min, the wells were washed with tap water, dried and the spots counted under a stereoscopic microscope (Leica Microscopy System, Heerbrugg, Switzerland). Alternatively, in some assays we used HRPO-labelled streptavidin (Amersham, UK), diluted 1/800; spots were then developed with 0.1% of 3,3'-diaminobenzidine (Sigma, Saint Louis, USA) in Tris-HCl 50 mM, pH 7.4 and 0.1% of hydrogen peroxide. The results were expressed as the number of spot-forming-cells (SFC) per $10^6$ splenocytes or fractionated cells. Values more than twice the negative control for each group (P815 without peptide or infected with control VV) were considered positive.

Figure 6:
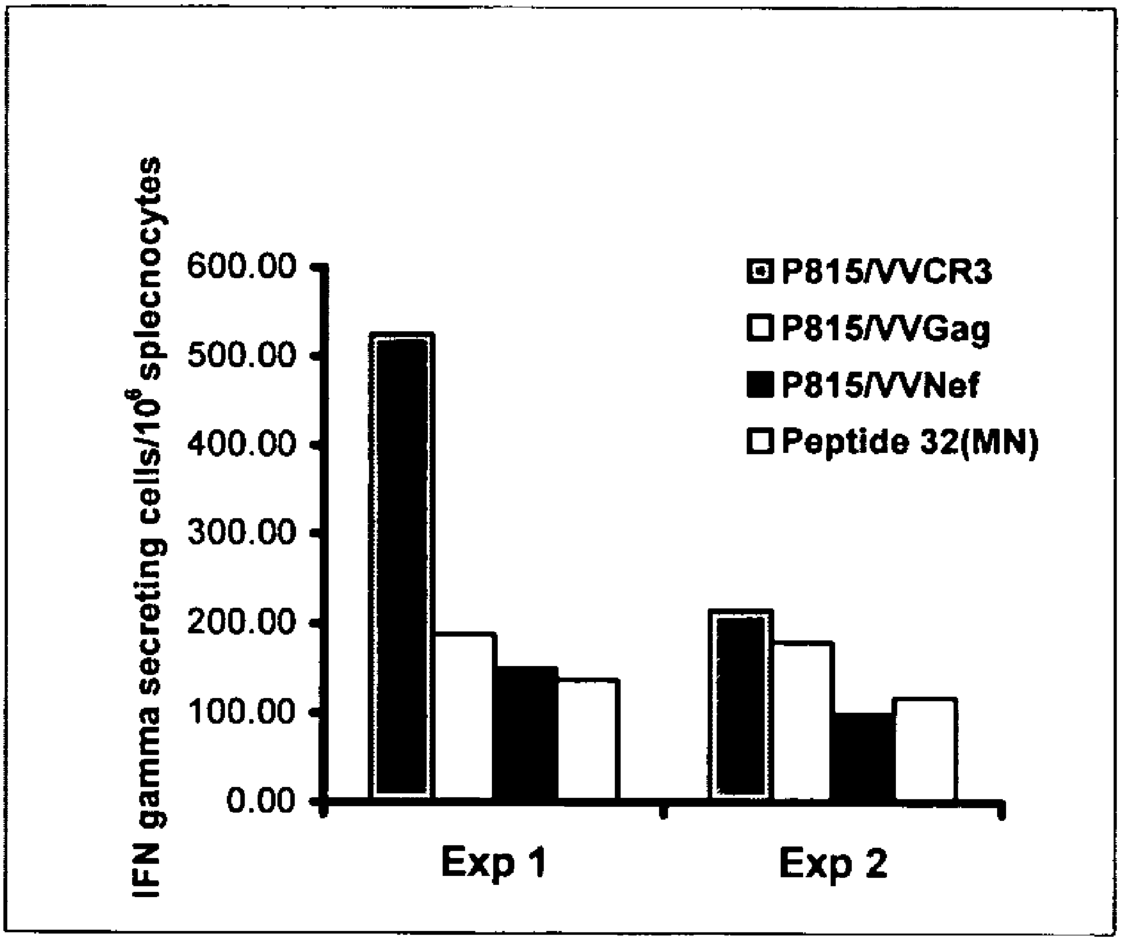
FIG. 6. Results from two independent ELISPOT experiments using splenocytes from mice immunized with FPSCR3gpt and P815 cells loaded with peptide 32 or infected with VV recombinant for CR3, Gag or Nef. The results are expressed as number of IFN gamma secreting cells per $10^6$ splenocytes. The values of the corresponding negative controls (P815 alone or VV WR infected) have been subtracted.

Results from two independent ELISPOT assay are shown in FIG. 6. A significant fraction of splenocytes from Balb/c mice immunized with FPCR3 but no with negative virus was positive in IFN gamma ELISPOT against P815 infected either with VVCR3 or VVgag and VVnef or primed with the V3 MN peptides (LKKKRIHIGPGRAFYERY) (SEQ. ID. NO:13).

Figure 7:
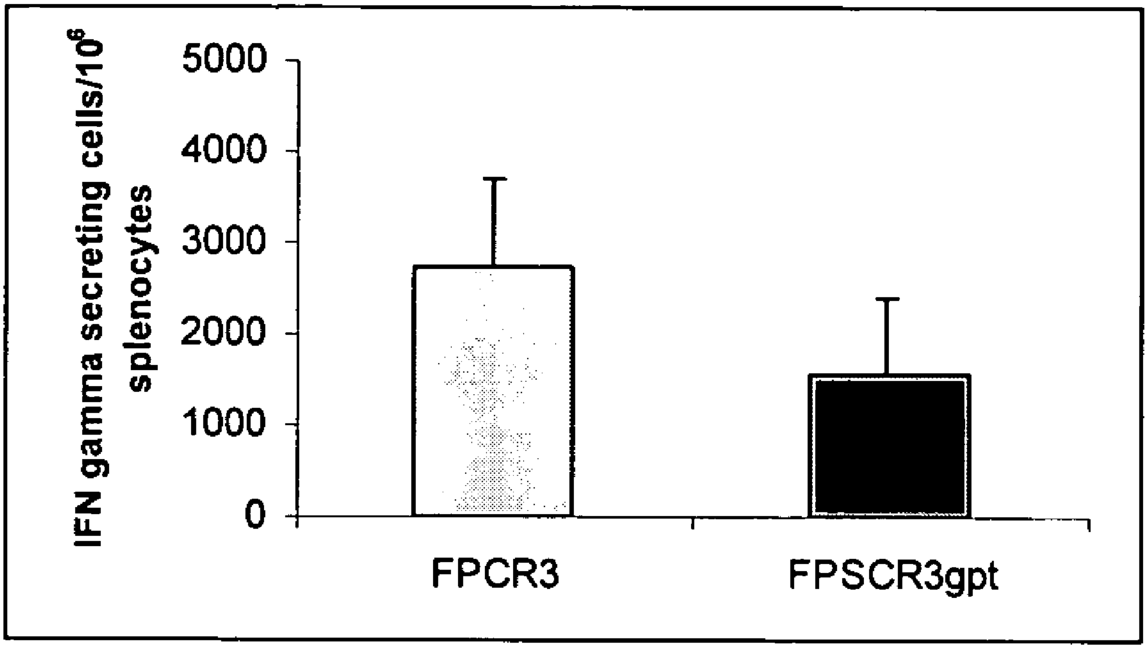
FIG. 7. IFN gamma ELISPOT experiments using splenocytes from mice immunized with FPCR3 or FPSCR3gpt and P815 stably transfected with the cr3 gene. The results are expressed as number of IFN gamma secreting cells per $10^6$ splenocytes. The values of the negative controls (parental P815) have been subtracted.
Figure 8:
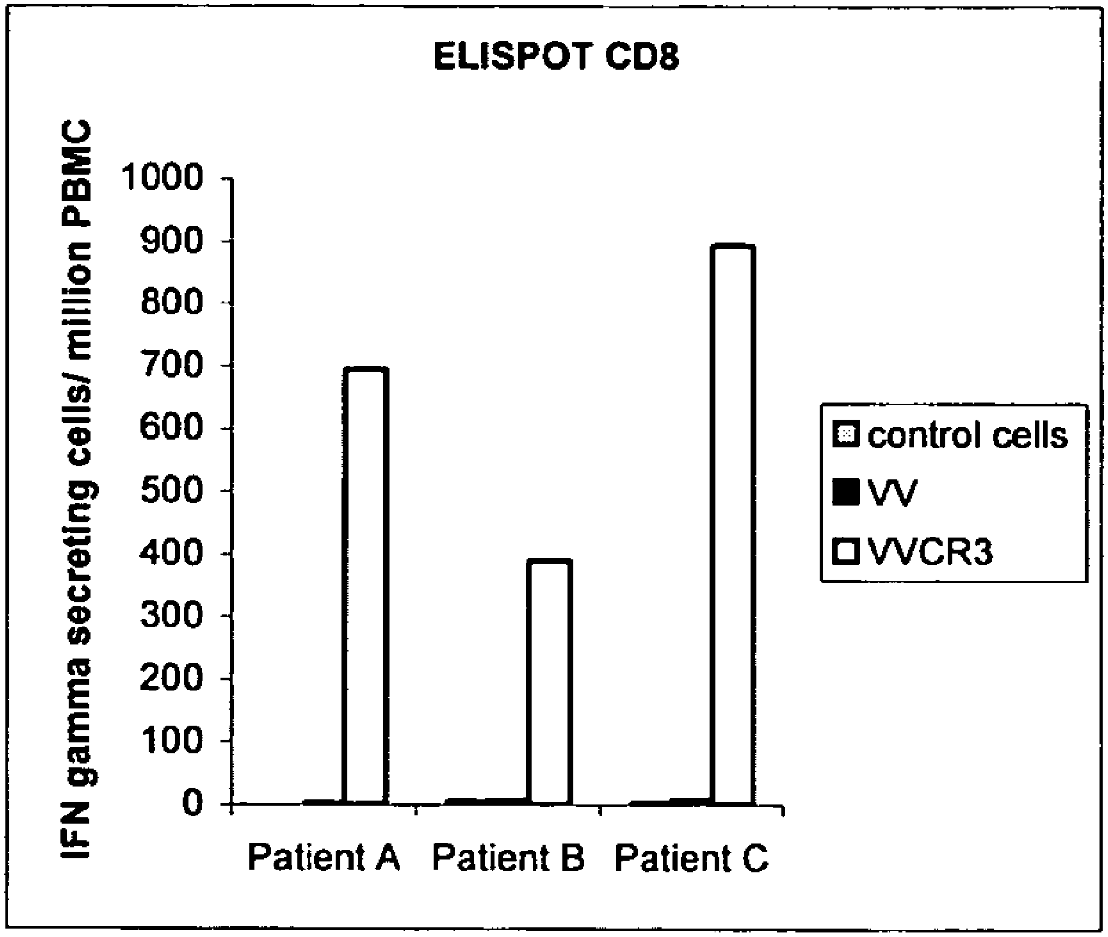
FIG. 8. Recognition of VVCR3 infected autologous B cells by T lymphocytes from AIDS patients. The results from an IFNγ ELISPOT are expressed as the number of IFN gamma secreting cells per $10^6$ peripheral blood mononuclear cells.

In another experiment Balb/c mice were immunized with FPCR3 or FPSCR3gpt as described and the induction of CTLs was measured using a P815 stably transfected with cr3 (P815cr3). The results from this experiment are show in FIG. 7. Both recombinant FPV induced a significant fraction of IFB gamma secreting cells specific for CR3.

Example 11

Proccesing and Recognition of CR3 Epitopes by Lymphocytes From AIDS Patients Autologous B cells from HIV infected patients were EBV transformed and infected with a VV recombinant for CR3 (VVCR3). Those targets cells were incubated with peripheral blood lymphocytes from HIV patients and the number of IFNγ secreting splenocytes were calculated by ELISPOT. This experiment demonstrated that cr3 gene expressed by poxvirus is capable to present efficiently its epitopes to CTL lymphocytes from HIV infected patients.

What is claimed is:

1. A chimeric protein encoded by a nucleic acid sequence comprising SEQ. ID. NO.: 1.

* * * * *

UNITED STATES PATENT AND TRADEMARK OFFICE

CERTIFICATE OF CORRECTION

PATENT NO. : 7,318,927 B2
APPLICATION NO. : 10/469256
DATED : January 15, 2008
INVENTOR(S) : Enrique Iglesias Perez et al.

It is certified that error appears in the above-identified patent and that said Letters Patent is hereby corrected as shown below:

ON THE TITLE PAGE ITEM (74)

now reads “Hoffman”
should read --Hoffmann--;

Column 7, line 42:

now reads: “under the control of W”

should read: --under the control of VV--

Signed and Sealed this

Second Day of September, 2008

JON W. DUDAS
*Director of the United States Patent and Trademark Office*

SEQUENCE LISTING

```
<160> NUMBER OF SEQ ID NOS: 96

<210> SEQ ID NO 1
<211> LENGTH: 1333
<212> TYPE: DNA
<213> ORGANISM: Human immunodeficiency virus type 1

<400> SEQUENCE: 1

atgcgtatca aacagattat caacatgtgg caggaagtgg gcaaagcgat gtatgccccg     60

ccgatttctg gtatggttga gcagatgcat gaagatatca ttagcctgtg ggaccagtct    120

cttaagaaaa agcgtatcca cattggccca ggccgtgcat tctatgaaag atacctaaag    180

gatcaacagc tcctagggaa aaagcaactg ctgtttattc atttcagaat tgggtgtcga    240

catagcagaa agaaagagat ctgtacagaa atggaaaagg aagggaaaat ttcaaaaatt    300

gggcctgaaa atccatacaa tactccagta tttgctataa agaaaaaaga cagtactaaa    360

tggagaaaac tagtagattt cagagaactt aataaaagaa ctcaagactt ctgggaagtt    420

cagttaggaa taccacaccc cgcagggtta aaaaagaaaa aatcagtaac agtattggat    480

gtgggtgatg catacttttc agttccctta gataaagact ttagaaagta tactgcattt    540

accataccta gtataaacaa tgagacacca gggattagat atcagtacaa tgtgctgcca    600

cagggatgga aaggatcacc agcaatattc caaagtagca tgacaaaaat cttagagcct    660

tttagaaaac agaatccaga catagttatc tatcaataca tggatgattt gtatgtagga    720

tcggacatca caagtagcaa tacagcagct accaatgctg attgtgcctg gctagaagca    780

caagaggagg aggagatggg ttttccagtc acacctcagg tacctttaag accaatgact    840

tacaaggcag ctgtagatct tagccacttt ttaaaagaaa aggggggact ggaagggcta    900

attcactccc aacgaagaca agatatcctt gatctgtgga tctaccacac acaaggctac    960
```

-continued

```
ttccctgatt ggcagaacta cacaccaggg ccaggggtca gatatccact gacctttgga   1020

tggtgctaca agctagtacc agttgagcca catgcagggc ctattgcacc aggccaaatg   1080

agagaaccaa ggggaagtga catagcagga actactagta cccttcagga acaaatagga   1140

tggatgacaa ataatccacc tatcccagta ggagaaatct ataaaagatg gataatcctg   1200

ggattaaata aaatagtaag aatgtatagc cctaccagct ttctggacat aagacaagga   1260

ccaaaggaac cctttagaga ttatgtagac cggttctata aaactctaag agccgaataa   1320

tctagaacgg atc                                                      1333
```

```
<210> SEQ ID NO 2
<211> LENGTH: 25
<212> TYPE: DNA
<213> ORGANISM: Human immunodeficiency virus type 1

<400> SEQUENCE: 2

gaagatctgt acagaaatgg aaaag                                           25


<210> SEQ ID NO 3
<211> LENGTH: 31
<212> TYPE: DNA
<213> ORGANISM: Human immunodeficiency virus type 1

<400> SEQUENCE: 3

ggaattctcg cgatcctaca tacaaatcat c                                    31


<210> SEQ ID NO 4
<211> LENGTH: 23
<212> TYPE: DNA
<213> ORGANISM: Human immunodeficiency virus type 1

<400> SEQUENCE: 4

gacatcacaa gtagcaatac agc                                             23


<210> SEQ ID NO 5
<211> LENGTH: 31
<212> TYPE: DNA
<213> ORGANISM: Human immunodeficiency virus type 1

<400> SEQUENCE: 5

ccctgcatgt ggctcaactg gtactagctt g                                    31


<210> SEQ ID NO 6
<211> LENGTH: 28
<212> TYPE: DNA
<213> ORGANISM: Human immunodeficiency virus type 1

<400> SEQUENCE: 6

gttgagccac atgcagggcc tattgcac                                        28


<210> SEQ ID NO 7
<211> LENGTH: 33
<212> TYPE: DNA
<213> ORGANISM: Human immunodeficiency virus type 1

<400> SEQUENCE: 7

gctctagatt attcggctct tagagtttta tag                                  33


<210> SEQ ID NO 8
<211> LENGTH: 25
<212> TYPE: DNA
<213> ORGANISM: Human immunodeficiency virus type 1
```

-continued

<400> SEQUENCE: 8
gctctagatt attcggctct tagag 25

<210> SEQ ID NO 9
<211> LENGTH: 19
<212> TYPE: DNA
<213> ORGANISM: Human immunodeficiency virus type 1

<400> SEQUENCE: 9
tattaacatt gcctagtag 19

<210> SEQ ID NO 10
<211> LENGTH: 20
<212> TYPE: DNA
<213> ORGANISM: Human immunodeficiency virus type 1

<400> SEQUENCE: 10
gaagtagaat cataaagaac 20

<210> SEQ ID NO 11
<211> LENGTH: 25
<212> TYPE: DNA
<213> ORGANISM: Human immunodeficiency virus type 1

<400> SEQUENCE: 11
gaagatctgt acagaaatgg aaaag 25

<210> SEQ ID NO 12
<211> LENGTH: 31
<212> TYPE: DNA
<213> ORGANISM: Human immunodeficiency virus type 1

<400> SEQUENCE: 12
ccctgcatgt ggctcaactg gtactagctt g 31

<210> SEQ ID NO 13
<211> LENGTH: 18
<212> TYPE: PRT
<213> ORGANISM: Human immunodeficiency virus type 1

<400> SEQUENCE: 13

Leu Lys Lys Lys Arg Ile His Ile Gly Pro Gly Arg Ala Phe Tyr Glu
1 5 10 15

Arg Tyr

<210> SEQ ID NO 14
<211> LENGTH: 15
<212> TYPE: PRT
<213> ORGANISM: Human immunodeficiency virus type 1

<400> SEQUENCE: 14

His Ala Gly Pro Ile Ala Pro Gly Gln Met Arg Glu Pro Arg Gly
1 5 10 15

<210> SEQ ID NO 15
<211> LENGTH: 20
<212> TYPE: PRT
<213> ORGANISM: Human immunodeficiency virus type 1

<400> SEQUENCE: 15

Ile Ala Pro Gly Gln Met Arg Glu Pro Arg Gly Ser Asp Ile Ala Gly
1 5 10 15

-continued

Thr Thr Ser Thr
20

<210> SEQ ID NO 16
<211> LENGTH: 20
<212> TYPE: PRT
<213> ORGANISM: Human immunodeficiency virus type 1

<400> SEQUENCE: 16

Gly Ser Asp Ile Ala Gly Thr Thr Ser Thr Leu Gln Glu Gln Ile Gly
1 5 10 15

Trp Met Thr Asn
20

<210> SEQ ID NO 17
<211> LENGTH: 10
<212> TYPE: PRT
<213> ORGANISM: Human immunodeficiency virus type 1

<400> SEQUENCE: 17

Thr Ser Thr Leu Gln Glu Gln Ile Gly Trp
1 5 10

<210> SEQ ID NO 18
<211> LENGTH: 15
<212> TYPE: PRT
<213> ORGANISM: Human immunodeficiency virus type 1

<400> SEQUENCE: 18

Asn Pro Pro Ile Pro Val Gly Glu Ile Tyr Lys Arg Trp Ile Ile
1 5 10 15

<210> SEQ ID NO 19
<211> LENGTH: 22
<212> TYPE: PRT
<213> ORGANISM: Human immunodeficiency virus type 1

<400> SEQUENCE: 19

Asn Pro Pro Ile Pro Val Gly Glu Ile Tyr Lys Arg Trp Ile Ile Leu
1 5 10 15

Gly Leu Asn Lys Ile Val
20

<210> SEQ ID NO 20
<211> LENGTH: 9
<212> TYPE: PRT
<213> ORGANISM: Human immunodeficiency virus type 1

<400> SEQUENCE: 20

Pro Pro Ile Pro Val Gly Glu Ile Tyr
1 5

<210> SEQ ID NO 21
<211> LENGTH: 15
<212> TYPE: PRT
<213> ORGANISM: Human immunodeficiency virus type 1

<400> SEQUENCE: 21

Ile Pro Val Gly Glu Ile Tyr Lys Arg Trp Ile Ile Leu Gly Leu
1 5 10 15

<210> SEQ ID NO 22
<211> LENGTH: 9

-continued

```
<212> TYPE: PRT
<213> ORGANISM: Human immunodeficiency virus type 1

<400> SEQUENCE: 22

Gly Glu Ile Tyr Lys Arg Trp Ile Ile
1               5


<210> SEQ ID NO 23
<211> LENGTH: 9
<212> TYPE: PRT
<213> ORGANISM: Human immunodeficiency virus type 1

<400> SEQUENCE: 23

Glu Ile Tyr Lys Arg Trp Ile Ile Leu
1               5


<210> SEQ ID NO 24
<211> LENGTH: 10
<212> TYPE: PRT
<213> ORGANISM: Human immunodeficiency virus type 1

<400> SEQUENCE: 24

Ile Tyr Lys Arg Trp Ile Ile Leu Gly Leu
1               5                   10


<210> SEQ ID NO 25
<211> LENGTH: 19
<212> TYPE: PRT
<213> ORGANISM: Human immunodeficiency virus type 1

<400> SEQUENCE: 25

Tyr Lys Arg Trp Ile Ile Leu Gly Leu Asn Lys Thr Val Arg Met Tyr
1               5                   10                  15

Ser Pro Thr


<210> SEQ ID NO 26
<211> LENGTH: 9
<212> TYPE: PRT
<213> ORGANISM: Human immunodeficiency virus type 1

<400> SEQUENCE: 26

Lys Arg Trp Ile Ile Leu Gly Leu Asn
1               5


<210> SEQ ID NO 27
<211> LENGTH: 10
<212> TYPE: PRT
<213> ORGANISM: Human immunodeficiency virus type 1

<400> SEQUENCE: 27

Ile Ile Leu Gly Leu Asn Lys Ile Val Arg
1               5                   10


<210> SEQ ID NO 28
<211> LENGTH: 10
<212> TYPE: PRT
<213> ORGANISM: Human immunodeficiency virus type 1

<400> SEQUENCE: 28

Leu Gly Leu Asn Lys Ile Val Arg Met Tyr
1               5                   10


<210> SEQ ID NO 29
<211> LENGTH: 11
```

-continued

```
<212> TYPE: PRT
<213> ORGANISM: Human immunodeficiency virus type 1

<400> SEQUENCE: 29

Leu Gly Leu Asn Lys Ile Val Arg Met Tyr Ser
1               5                   10


<210> SEQ ID NO 30
<211> LENGTH: 9
<212> TYPE: PRT
<213> ORGANISM: Human immunodeficiency virus type 1

<400> SEQUENCE: 30

Gly Leu Asn Lys Ile Val Arg Met Tyr
1               5


<210> SEQ ID NO 31
<211> LENGTH: 19
<212> TYPE: PRT
<213> ORGANISM: Human immunodeficiency virus type 1

<400> SEQUENCE: 31

Leu Asp Ile Arg Gln Gly Pro Lys Glu Pro Arg Asp Tyr Val Asp Arg
1               5                   10                  15

Phe Tyr Lys


<210> SEQ ID NO 32
<211> LENGTH: 11
<212> TYPE: PRT
<213> ORGANISM: Human immunodeficiency virus type 1

<400> SEQUENCE: 32

Arg Asp Tyr Val Asp Arg Phe Tyr Lys Thr Leu
1               5                   10


<210> SEQ ID NO 33
<211> LENGTH: 9
<212> TYPE: PRT
<213> ORGANISM: Human immunodeficiency virus type 1

<400> SEQUENCE: 33

Asp Arg Phe Tyr Lys Thr Leu Arg Ala
1               5


<210> SEQ ID NO 34
<211> LENGTH: 9
<212> TYPE: PRT
<213> ORGANISM: Human immunodeficiency virus type 1

<400> SEQUENCE: 34

Phe Pro Val Thr Pro Gln Val Pro Leu
1               5


<210> SEQ ID NO 35
<211> LENGTH: 10
<212> TYPE: PRT
<213> ORGANISM: Human immunodeficiency virus type 1

<400> SEQUENCE: 35

Phe Pro Val Thr Pro Gln Val Pro Leu Arg
1               5                   10


<210> SEQ ID NO 36
<211> LENGTH: 9
```

-continued

<212> TYPE: PRT
<213> ORGANISM: Human immunodeficiency virus type 1

<400> SEQUENCE: 36

Thr Pro Gln Val Pro Leu Arg Pro Met
1 5

<210> SEQ ID NO 37
<211> LENGTH: 8
<212> TYPE: PRT
<213> ORGANISM: Human immunodeficiency virus type 1

<400> SEQUENCE: 37

Val Pro Leu Arg Pro Met Thr Tyr
1 5

<210> SEQ ID NO 38
<211> LENGTH: 10
<212> TYPE: PRT
<213> ORGANISM: Human immunodeficiency virus type 1

<400> SEQUENCE: 38

Gln Val Pro Leu Arg Pro Met Thr Tyr Lys
1 5 10

<210> SEQ ID NO 39
<211> LENGTH: 8
<212> TYPE: PRT
<213> ORGANISM: Human immunodeficiency virus type 1

<400> SEQUENCE: 39

Val Pro Leu Arg Pro Met Thr Tyr
1 5

<210> SEQ ID NO 40
<211> LENGTH: 8
<212> TYPE: PRT
<213> ORGANISM: Human immunodeficiency virus type 1

<400> SEQUENCE: 40

Pro Leu Arg Pro Met Thr Tyr Lys
1 5

<210> SEQ ID NO 41
<211> LENGTH: 10
<212> TYPE: PRT
<213> ORGANISM: Human immunodeficiency virus type 1

<400> SEQUENCE: 41

Lys Ala Ala Val Asp Leu Ser His Phe Leu
1 5 10

<210> SEQ ID NO 42
<211> LENGTH: 12
<212> TYPE: PRT
<213> ORGANISM: Human immunodeficiency virus type 1

<400> SEQUENCE: 42

Ala Ala Val Asp Leu Ser His Phe Leu Lys Glu Lys
1 5 10

<210> SEQ ID NO 43
<211> LENGTH: 8
<212> TYPE: PRT
<213> ORGANISM: Human immunodeficiency virus type 1

-continued

<400> SEQUENCE: 43

Ala Val Asp Leu Ser His Phe Leu
1 5

<210> SEQ ID NO 44
<211> LENGTH: 9
<212> TYPE: PRT
<213> ORGANISM: Human immunodeficiency virus type 1

<400> SEQUENCE: 44

Ala Val Asp Leu Ser His Phe Leu Lys
1 5

<210> SEQ ID NO 45
<211> LENGTH: 9
<212> TYPE: PRT
<213> ORGANISM: Human immunodeficiency virus type 1

<400> SEQUENCE: 45

Asp Leu Ser His Phe Leu Lys Glu Lys
1 5

<210> SEQ ID NO 46
<211> LENGTH: 15
<212> TYPE: PRT
<213> ORGANISM: Human immunodeficiency virus type 1

<400> SEQUENCE: 46

Asp Leu Ser His Phe Leu Lys Glu Lys Gly Gly Leu Glu Gly Leu
1 5 10 15

<210> SEQ ID NO 47
<211> LENGTH: 8
<212> TYPE: PRT
<213> ORGANISM: Human immunodeficiency virus type 1

<400> SEQUENCE: 47

Phe Leu Lys Glu Lys Gly Gly Leu
1 5

<210> SEQ ID NO 48
<211> LENGTH: 9
<212> TYPE: PRT
<213> ORGANISM: Human immunodeficiency virus type 1

<400> SEQUENCE: 48

Lys Glu Lys Gly Gly Leu Glu Gly Leu
1 5

<210> SEQ ID NO 49
<211> LENGTH: 14
<212> TYPE: PRT
<213> ORGANISM: Human immunodeficiency virus type 1

<400> SEQUENCE: 49

Glu Lys Gly Gly Leu Glu Gly Leu Ile His Ser Gln Arg Arg
1 5 10

<210> SEQ ID NO 50
<211> LENGTH: 14
<212> TYPE: PRT
<213> ORGANISM: Human immunodeficiency virus type 1

<400> SEQUENCE: 50

-continued

His Ser Gln Arg Arg Gln Asp Ile Leu Asp Leu Trp Ile Tyr
1 5 10

<210> SEQ ID NO 51
<211> LENGTH: 25
<212> TYPE: PRT
<213> ORGANISM: Human immunodeficiency virus type 1

<400> SEQUENCE: 51

Ser Gln Arg Arg Gln Asp Ile Leu Asp Leu Trp Ile Tyr His Thr Gln
1 5 10 15

Gly Tyr Phe Pro Asp Trp Gln Asn Tyr
20 25

<210> SEQ ID NO 52
<211> LENGTH: 10
<212> TYPE: PRT
<213> ORGANISM: Human immunodeficiency virus type 1

<400> SEQUENCE: 52

Arg Arg Gln Asp Ile Leu Asp Leu Trp Ile
1 5 10

<210> SEQ ID NO 53
<211> LENGTH: 10
<212> TYPE: PRT
<213> ORGANISM: Human immunodeficiency virus type 1

<400> SEQUENCE: 53

Arg Gln Asp Ile Leu Asp Leu Trp Ile Tyr
1 5 10

<210> SEQ ID NO 54
<211> LENGTH: 11
<212> TYPE: PRT
<213> ORGANISM: Human immunodeficiency virus type 1

<400> SEQUENCE: 54

Tyr His Thr Gln Gly Tyr Phe Pro Asp Trp Gln
1 5 10

<210> SEQ ID NO 55
<211> LENGTH: 10
<212> TYPE: PRT
<213> ORGANISM: Human immunodeficiency virus type 1

<400> SEQUENCE: 55

His Thr Gln Gly Tyr Phe Pro Asp Trp Gln
1 5 10

<210> SEQ ID NO 56
<211> LENGTH: 12
<212> TYPE: PRT
<213> ORGANISM: Human immunodeficiency virus type 1

<400> SEQUENCE: 56

Thr Gln Gly Tyr Phe Pro Asp Trp Gln Asn Tyr Thr
1 5 10

<210> SEQ ID NO 57
<211> LENGTH: 11
<212> TYPE: PRT
<213> ORGANISM: Human immunodeficiency virus type 1

-continued

<400> SEQUENCE: 57

Thr Gln Gly Tyr Phe Pro Asp Trp Gln Asn Tyr
1 5 10

<210> SEQ ID NO 58
<211> LENGTH: 9
<212> TYPE: PRT
<213> ORGANISM: Human immunodeficiency virus type 1

<400> SEQUENCE: 58

Tyr Phe Pro Asp Trp Gln Asn Tyr Thr
1 5

<210> SEQ ID NO 59
<211> LENGTH: 25
<212> TYPE: PRT
<213> ORGANISM: Human immunodeficiency virus type 1

<400> SEQUENCE: 59

Tyr Phe Pro Asp Trp Gln Asn Tyr Thr Pro Gly Pro Gly Ile Arg Tyr
1 5 10 15

Pro Leu Thr Phe Gly Trp Cys Tyr Lys
20 25

<210> SEQ ID NO 60
<211> LENGTH: 13
<212> TYPE: PRT
<213> ORGANISM: Human immunodeficiency virus type 1

<400> SEQUENCE: 60

Asn Tyr Thr Pro Gly Pro Gly Val Arg Tyr Pro Leu Thr
1 5 10

<210> SEQ ID NO 61
<211> LENGTH: 11
<212> TYPE: PRT
<213> ORGANISM: Human immunodeficiency virus type 1

<400> SEQUENCE: 61

Thr Pro Gly Pro Gly Val Arg Tyr Pro Leu Thr
1 5 10

<210> SEQ ID NO 62
<211> LENGTH: 14
<212> TYPE: PRT
<213> ORGANISM: Human immunodeficiency virus type 1

<400> SEQUENCE: 62

Gly Pro Gly Val Arg Tyr Pro Leu Thr Phe Gly Trp Cys Tyr
1 5 10

<210> SEQ ID NO 63
<211> LENGTH: 16
<212> TYPE: PRT
<213> ORGANISM: Human immunodeficiency virus type 1

<400> SEQUENCE: 63

Gly Val Arg Tyr Pro Leu Thr Phe Gly Trp Cys Tyr Lys Leu Val Pro
1 5 10 15

<210> SEQ ID NO 64
<211> LENGTH: 16
<212> TYPE: PRT
<213> ORGANISM: Human immunodeficiency virus type 1

-continued

<400> SEQUENCE: 64

Val Arg Tyr Pro Leu Thr Phe Gly Trp Cys Tyr Lys Leu Val Pro Val
1 5 10 15

<210> SEQ ID NO 65
<211> LENGTH: 9
<212> TYPE: PRT
<213> ORGANISM: Human immunodeficiency virus type 1

<400> SEQUENCE: 65

Tyr Pro Leu Thr Phe Gly Trp Cys Tyr
1 5

<210> SEQ ID NO 66
<211> LENGTH: 10
<212> TYPE: PRT
<213> ORGANISM: Human immunodeficiency virus type 1

<400> SEQUENCE: 66

Pro Leu Thr Phe Gly Trp Cys Tyr Lys Leu
1 5 10

<210> SEQ ID NO 67
<211> LENGTH: 17
<212> TYPE: PRT
<213> ORGANISM: Human immunodeficiency virus type 1

<400> SEQUENCE: 67

Glu Ile Cys Thr Glu Met Glu Lys Glu Gly Lys Ile Ser Lys Ile Gly
1 5 10 15

Pro

<210> SEQ ID NO 68
<211> LENGTH: 9
<212> TYPE: PRT
<213> ORGANISM: Human immunodeficiency virus type 1

<400> SEQUENCE: 68

Glu Lys Glu Gly Lys Ile Ser Lys Ile
1 5

<210> SEQ ID NO 69
<211> LENGTH: 9
<212> TYPE: PRT
<213> ORGANISM: Human immunodeficiency virus type 1

<400> SEQUENCE: 69

Gly Ile Pro His Pro Ala Gly Leu Lys
1 5

<210> SEQ ID NO 70
<211> LENGTH: 16
<212> TYPE: PRT
<213> ORGANISM: Human immunodeficiency virus type 1

<400> SEQUENCE: 70

Ala Gly Leu Lys Lys Lys Lys Ser Val Thr Val Leu Asp Val Gly Asp
1 5 10 15

<210> SEQ ID NO 71
<211> LENGTH: 15
<212> TYPE: PRT
<213> ORGANISM: Human immunodeficiency virus type 1

<400> SEQUENCE: 71

Lys Lys Ser Val Thr Val Leu Asp Val Gly Asp Ala Tyr Phe Ser
1 5 10 15

<210> SEQ ID NO 72
<211> LENGTH: 9
<212> TYPE: PRT
<213> ORGANISM: Human immunodeficiency virus type 1

<400> SEQUENCE: 72

Thr Val Leu Asp Val Gly Asp Ala Tyr
1 5

<210> SEQ ID NO 73
<211> LENGTH: 11
<212> TYPE: PRT
<213> ORGANISM: Human immunodeficiency virus type 1

<400> SEQUENCE: 73

Val Leu Asp Val Gly Asp Ala Tyr Phe Ser Val
1 5 10

<210> SEQ ID NO 74
<211> LENGTH: 8
<212> TYPE: PRT
<213> ORGANISM: Human immunodeficiency virus type 1

<400> SEQUENCE: 74

Asp Ala Tyr Phe Ser Val Pro Leu
1 5

<210> SEQ ID NO 75
<211> LENGTH: 10
<212> TYPE: PRT
<213> ORGANISM: Human immunodeficiency virus type 1

<400> SEQUENCE: 75

Val Pro Leu Asp Glu Asp Phe Arg Lys Tyr
1 5 10

<210> SEQ ID NO 76
<211> LENGTH: 10
<212> TYPE: PRT
<213> ORGANISM: Human immunodeficiency virus type 1

<400> SEQUENCE: 76

Lys Tyr Thr Ala Phe Thr Ile Pro Ser Ile
1 5 10

<210> SEQ ID NO 77
<211> LENGTH: 8
<212> TYPE: PRT
<213> ORGANISM: Human immunodeficiency virus type 1

<400> SEQUENCE: 77

Thr Ala Phe Thr Ile Pro Ser Ile
1 5

<210> SEQ ID NO 78
<211> LENGTH: 9
<212> TYPE: PRT
<213> ORGANISM: Human immunodeficiency virus type 1

<400> SEQUENCE: 78

-continued

Gln Gly Trp Lys Gly Ser Pro Ala Ile
1 5

<210> SEQ ID NO 79
<211> LENGTH: 13
<212> TYPE: PRT
<213> ORGANISM: Human immunodeficiency virus type 1

<400> SEQUENCE: 79

Trp Lys Gly Ser Pro Ala Ile Phe Gln Ser Ser Met Thr
1 5 10

<210> SEQ ID NO 80
<211> LENGTH: 9
<212> TYPE: PRT
<213> ORGANISM: Human immunodeficiency virus type 1

<400> SEQUENCE: 80

Ser Pro Ala Ile Phe Gln Ser Ser Met
1 5

<210> SEQ ID NO 81
<211> LENGTH: 9
<212> TYPE: PRT
<213> ORGANISM: Human immunodeficiency virus type 1

<400> SEQUENCE: 81

Ala Ile Phe Gln Ser Ser Met Thr Lys
1 5

<210> SEQ ID NO 82
<211> LENGTH: 9
<212> TYPE: PRT
<213> ORGANISM: Human immunodeficiency virus type 1

<400> SEQUENCE: 82

Lys Gln Asn Pro Asp Ile Val Ile Tyr
1 5

<210> SEQ ID NO 83
<211> LENGTH: 9
<212> TYPE: PRT
<213> ORGANISM: Human immunodeficiency virus type 1

<400> SEQUENCE: 83

Asn Pro Asp Ile Val Ile Tyr Gln Tyr
1 5

<210> SEQ ID NO 84
<211> LENGTH: 9
<212> TYPE: PRT
<213> ORGANISM: Human immunodeficiency virus type 1

<400> SEQUENCE: 84

Val Ile Tyr Gln Tyr Met Asp Asp Leu
1 5

<210> SEQ ID NO 85
<211> LENGTH: 11
<212> TYPE: PRT
<213> ORGANISM: Human immunodeficiency virus type 1

<400> SEQUENCE: 85

Val Ile Tyr Gln Tyr Met Asp Asp Leu Tyr Val

-continued 1 5 10

<210> SEQ ID NO 86
<211> LENGTH: 20
<212> TYPE: PRT
<213> ORGANISM: Human immunodeficiency virus type 1

<400> SEQUENCE: 86

Phe Arg Lys Gln Asn Pro Asp Ile Val Ile Tyr Gln Tyr Met Asp Asp
1 5 10 15

Leu Tyr Val Gly
20

<210> SEQ ID NO 87
<211> LENGTH: 20
<212> TYPE: PRT
<213> ORGANISM: Human immunodeficiency virus type 1

<400> SEQUENCE: 87

Lys Gln Ile Ile Asn Met Trp Gln Glu Val Gly Lys Ala Met Tyr Ala
1 5 10 15

Pro Pro Ile Glu
20

<210> SEQ ID NO 88
<211> LENGTH: 7
<212> TYPE: PRT
<213> ORGANISM: Human immunodeficiency virus type 1

<400> SEQUENCE: 88

Lys Val Gly Lys Ala Met Tyr
1 5

<210> SEQ ID NO 89
<211> LENGTH: 8
<212> TYPE: PRT
<213> ORGANISM: Human immunodeficiency virus type 1

<400> SEQUENCE: 89

Lys Val Gly Lys Ala Met Tyr Ala
1 5

<210> SEQ ID NO 90
<211> LENGTH: 13
<212> TYPE: PRT
<213> ORGANISM: Human immunodeficiency virus type 1

<400> SEQUENCE: 90

His Glu Asp Ile Ile Ser Leu Trp Asn Gln Ser Leu Lys
1 5 10

<210> SEQ ID NO 91
<211> LENGTH: 9
<212> TYPE: PRT
<213> ORGANISM: Human immunodeficiency virus type 1

<400> SEQUENCE: 91

Ile Ile Ser Leu Trp Asn Gln Ser Leu
1 5

<210> SEQ ID NO 92
<211> LENGTH: 11
<212> TYPE: PRT
<213> ORGANISM: Human immunodeficiency virus type 1

-continued

<400> SEQUENCE: 92

Glu Arg Tyr Leu Lys Asp Gln Gln Leu Leu Gly
1               5                   10

<210> SEQ ID NO 93
<211> LENGTH: 8
<212> TYPE: PRT
<213> ORGANISM: Human immunodeficiency virus type 1

<400> SEQUENCE: 93

Tyr Leu Lys Asp Gln Gln Leu Leu
1               5

<210> SEQ ID NO 94
<211> LENGTH: 10
<212> TYPE: PRT
<213> ORGANISM: Human immunodeficiency virus type 1

<400> SEQUENCE: 94

Glu Arg Tyr Leu Lys Asp Gln Gln Leu Leu
1               5                   10

<210> SEQ ID NO 95
<211> LENGTH: 8
<212> TYPE: PRT
<213> ORGANISM: Human immunodeficiency virus type 1

<400> SEQUENCE: 95

Arg Tyr Leu Lys Asp Gln Gln Leu
1               5

<210> SEQ ID NO 96
<211> LENGTH: 15
<212> TYPE: PRT
<213> ORGANISM: Human immunodeficiency virus type 1

<400> SEQUENCE: 96

Gln Leu Leu Phe Ile His Phe Arg Ile Gly Cys Arg His Ser Arg
1               5                   10                  15